(12) United States Patent
Edman et al.

(10) Patent No.: US 8,690,769 B2
(45) Date of Patent: Apr. 8, 2014

(54) METABOLIC ENERGY MONITORING SYSTEM

(75) Inventors: Carl Frederick Edman, San Diego, CA (US); Naresh Chandra Bhavaraju, San Diego, CA (US); Darrel Dean Drinan, San Diego, CA (US)

(73) Assignee: PhiloMetron, Inc., San Diego, CA (US)

( * ) Notice: Subject to any disclaimer, the term of this patent is extended or adjusted under 35 U.S.C. 154(b) by 220 days.

(21) Appl. No.: 12/386,614

(22) Filed: Apr. 21, 2009

(65) Prior Publication Data

US 2010/0049004 A1 Feb. 25, 2010

Related U.S. Application Data

(60) Provisional application No. 61/125,140, filed on Apr. 21, 2008, provisional application No. 61/134,987, filed on Jul. 16, 2008, provisional application No. 61/206,423, filed on Jan. 31, 2009.

(51) Int. Cl.
*A61B 5/00* (2006.01)

(52) U.S. Cl.
USPC .......................................... 600/300; 128/920

(58) Field of Classification Search
None
See application file for complete search history.

(56) References Cited

U.S. PATENT DOCUMENTS

| | | | |
|---|---|---|---|
| 4,402,694 A | 9/1983 | Ash et al. | |
| 4,805,621 A | 2/1989 | Heinze et al. | |
| 4,854,328 A | 8/1989 | Pollack | |
| 4,860,753 A | 8/1989 | Amerena | |
| 4,870,753 A | 10/1989 | Pfeffer et al. | |
| 4,958,638 A | 9/1990 | Sharpe et al. | |
| 4,966,158 A | 10/1990 | Honma et al. | |
| 5,001,436 A | 3/1991 | Scot et al. | |
| 5,038,109 A | 8/1991 | Goble et al. | |
| 5,086,781 A | 2/1992 | Bookspan | |
| 5,242,415 A | 9/1993 | Kantrowitz et al. | |
| 5,297,556 A | 3/1994 | Shankar | |
| 5,335,667 A | 8/1994 | Cha et al. | |
| 5,353,802 A | 10/1994 | Ollmar | |
| 5,375,604 A | 12/1994 | Kelly et al. | |

(Continued)

FOREIGN PATENT DOCUMENTS

| | | |
|---|---|---|
| DE | 10008886 A1 | 9/2001 |
| EP | 1072994 A2 | 1/2001 |

(Continued)

OTHER PUBLICATIONS

BIOMEC Inc. Pneumothorax Detector. White paper, 2005.

(Continued)

*Primary Examiner* — Bill Thomson
*Assistant Examiner* — Davin K Sands

(57) ABSTRACT

A metabolic energy monitoring system having one or more physiological measurement platforms and displays enabling the calculation and display of energy balance, kilocalorie energy expenditure and kilocalorie intake is described. In preferred embodiments, the system utilizes one or more on-body monitoring platforms to enable measurement of change in body composition and kilocalorie energy expenditure over a period of time thereby enabling a comparator to calculate net energy balance over this period of time and to calculate kilocalorie intake over this same period of time. Such data may then be displayed on a display device in wireless communication with the on-body monitoring platform to provide the user of the system with useful information and guidance in weight management applications.

21 Claims, 6 Drawing Sheets

(56) References Cited

U.S. PATENT DOCUMENTS

| | | |
|---|---|---|
| 5,445,008 A | 8/1995 | Wachter et al. |
| 5,511,553 A | 4/1996 | Segalowitz |
| 5,558,638 A | 9/1996 | Evers et al. |
| 5,573,012 A | 11/1996 | McEwan |
| 5,634,468 A | 6/1997 | Platt et al. |
| 5,720,770 A | 2/1998 | Nappholz et al. |
| 5,732,710 A | 3/1998 | Rabinovich et al. |
| 5,738,107 A | 4/1998 | Martinsen et al. |
| 5,749,369 A | 5/1998 | Rabinovich et al. |
| 5,752,976 A | 5/1998 | Duffin et al. |
| 5,766,208 A | 6/1998 | McEwan |
| 5,779,630 A | 7/1998 | Fein et al. |
| 5,788,643 A | 8/1998 | Feldman |
| 5,829,437 A | 11/1998 | Bridges |
| 5,833,603 A | 11/1998 | Kovacs et al. |
| 5,879,292 A | 3/1999 | Sternberg et al. |
| 5,931,764 A | 8/1999 | Freeman et al. |
| 5,935,066 A | 8/1999 | Harris |
| 5,941,829 A | 8/1999 | Saltzstein et al. |
| 5,944,659 A | 8/1999 | Flach et al. |
| 5,964,703 A | 10/1999 | Goodman et al. |
| 5,964,720 A | 10/1999 | Pelz |
| 5,980,429 A | 11/1999 | Nashner |
| 5,987,352 A | 11/1999 | Klein et al. |
| 6,010,465 A | 1/2000 | Nashner |
| 6,016,686 A | 1/2000 | Thundat |
| 6,026,173 A | 2/2000 | Svenson et al. |
| 6,044,846 A | 4/2000 | Edwards |
| 6,047,203 A | 4/2000 | Sackner et al. |
| 6,074,345 A | 6/2000 | van Oostrom et al. |
| 6,083,248 A | 7/2000 | Thompson |
| 6,092,530 A | 7/2000 | Weissman et al. |
| 6,093,146 A | 7/2000 | Filangeri |
| 6,095,987 A | 8/2000 | Shmulewitz et al. |
| 6,125,297 A | 9/2000 | Siconolfi |
| 6,175,752 B1 | 1/2001 | Say et al. |
| 6,198,394 B1 | 3/2001 | Jacobsen et al. |
| 6,200,266 B1 | 3/2001 | Shokrollahi et al. |
| 6,213,942 B1 | 4/2001 | Flach et al. |
| 6,225,901 B1 | 5/2001 | Kail, IV |
| 6,244,873 B1 | 6/2001 | Hill et al. |
| 6,265,978 B1 | 7/2001 | Atlas |
| 6,287,252 B1 | 9/2001 | Lugo |
| 6,289,238 B1 | 9/2001 | Besson et al. |
| 6,315,719 B1 | 11/2001 | Rode et al. |
| 6,331,160 B1 | 12/2001 | Bardy |
| 6,339,722 B1 | 1/2002 | Heethaar et al. |
| 6,358,201 B1 | 3/2002 | Childre et al. |
| 6,360,888 B1 | 3/2002 | McIvor et al. |
| 6,370,426 B1 | 4/2002 | Campbell et al. |
| 6,411,853 B1 | 6/2002 | Millot et al. |
| 6,413,255 B1 | 7/2002 | Stern |
| 6,416,471 B1 | 7/2002 | Kumar et al. |
| 6,441,747 B1 | 8/2002 | Khair et al. |
| 6,454,711 B1 | 9/2002 | Haddad et al. |
| 6,459,917 B1 | 10/2002 | Gowda et al. |
| 6,459,930 B1 | 10/2002 | Takehara et al. |
| 6,482,158 B2 | 11/2002 | Mault |
| 6,496,705 B1 | 12/2002 | Ng et al. |
| 6,506,152 B1 | 1/2003 | Lackey et al. |
| 6,512,949 B1 | 1/2003 | Combs et al. |
| 6,524,239 B1 | 2/2003 | Reed et al. |
| 6,540,672 B1 | 4/2003 | Simonsen et al. |
| 6,544,174 B2 | 4/2003 | West et al. |
| 6,551,252 B2 | 4/2003 | Sackner et al. |
| 6,554,798 B1 | 4/2003 | Mann et al. |
| 6,577,893 B1 | 6/2003 | Besson et al. |
| 6,591,122 B2 | 7/2003 | Schmitt |
| 6,595,929 B2 | 7/2003 | Stivoric et al. |
| 6,605,038 B1 | 8/2003 | Teller et al. |
| 6,615,077 B1 | 9/2003 | Zhu et al. |
| 6,631,292 B1 | 10/2003 | Liedtke |
| 6,632,158 B1 | 10/2003 | Nashner |
| 6,636,754 B1 | 10/2003 | Baura et al. |
| 6,643,543 B2 | 11/2003 | Takehara et al. |
| 6,645,142 B2 | 11/2003 | Braig et al. |
| 6,699,188 B2 | 3/2004 | Wessel |
| 6,714,813 B2 | 3/2004 | Ishigooka et al. |
| 6,790,178 B1 | 9/2004 | Mault et al. |
| 6,823,212 B2 | 11/2004 | Pinyayev |
| 6,849,046 B1 | 2/2005 | Eyal-Bickels et al. |
| 6,897,788 B2 | 5/2005 | Khair et al. |
| 6,963,035 B2* | 11/2005 | Honda et al. ............... 177/25.19 |
| 6,963,772 B2 | 11/2005 | Bloom et al. |
| 6,980,852 B2 | 12/2005 | Jersey-Willuhn et al. |
| 7,010,339 B2 | 3/2006 | Mullen et al. |
| 7,040,168 B1 | 5/2006 | Merkel |
| 7,044,911 B2 | 5/2006 | Drinan et al. |
| 7,079,899 B2 | 7/2006 | Petrofsky |
| 7,089,047 B2 | 8/2006 | Holmes |
| 7,184,824 B2 | 2/2007 | Hashimshony |
| 7,191,000 B2 | 3/2007 | Zhu et al. |
| 7,239,902 B2 | 7/2007 | Schmitt et al. |
| 7,261,690 B2 | 8/2007 | Teller et al. |
| 7,280,863 B2 | 10/2007 | Shachar |
| 7,285,090 B2 | 10/2007 | Stivoric et al. |
| 7,499,745 B2 | 3/2009 | Littrup et al. |
| 7,889,069 B2 | 2/2011 | Fifolt et al. |
| 2001/0051774 A1 | 12/2001 | Littrup et al. |
| 2002/0019584 A1 | 2/2002 | Schulze et al. |
| 2002/0019586 A1 | 2/2002 | Teller et al. |
| 2002/0022773 A1* | 2/2002 | Drinan et al. ............... 600/300 |
| 2002/0045836 A1 | 4/2002 | Alkawwas |
| 2002/0133378 A1* | 9/2002 | Mault et al. ................... 705/3 |
| 2002/0156351 A1 | 10/2002 | Sagel |
| 2003/0004403 A1 | 1/2003 | Drinan et al. |
| 2003/0036674 A1 | 2/2003 | Bouton |
| 2003/0088180 A1 | 5/2003 | Van Veen et al. |
| 2003/0120170 A1 | 6/2003 | Zhu et al. |
| 2003/0149344 A1 | 8/2003 | Nizan |
| 2003/0199783 A1 | 10/2003 | Bloom et al. |
| 2003/0223905 A1 | 12/2003 | Moerman |
| 2004/0019292 A1 | 1/2004 | Drinan et al. |
| 2004/0030258 A1 | 2/2004 | Williams et al. |
| 2004/0039254 A1 | 2/2004 | Stivoric et al. |
| 2004/0077934 A1 | 4/2004 | Massad |
| 2004/0122353 A1 | 6/2004 | Shahmirian et al. |
| 2004/0127895 A1 | 7/2004 | Flock et al. |
| 2004/0133081 A1* | 7/2004 | Teller et al. .................. 600/300 |
| 2004/0147977 A1 | 7/2004 | Petrofsky |
| 2004/0152957 A1* | 8/2004 | Stivoric et al. ............... 600/300 |
| 2004/0152988 A1 | 8/2004 | Weirich |
| 2004/0171962 A1 | 9/2004 | Leveque et al. |
| 2004/0254457 A1 | 12/2004 | Van Der Weide |
| 2004/0254624 A1 | 12/2004 | Johnson |
| 2005/0021372 A1 | 1/2005 | Mikkelsen et al. |
| 2005/0070778 A1 | 3/2005 | Lackey et al. |
| 2005/0113650 A1* | 5/2005 | Pacione et al. ............... 600/300 |
| 2005/0179578 A1 | 8/2005 | Healy et al. |
| 2006/0025661 A1 | 2/2006 | Sweeney et al. |
| 2006/0052678 A1 | 3/2006 | Drinan et al. |
| 2006/0058593 A1 | 3/2006 | Drinan et al. |
| 2006/0089592 A1 | 4/2006 | Kadhiresan et al. |
| 2006/0264775 A1 | 11/2006 | Mills et al. |
| 2006/0270942 A1 | 11/2006 | McAdams |
| 2007/0048691 A1 | 3/2007 | Brown |
| 2007/0100666 A1 | 5/2007 | Stivoric et al. |
| 2007/0219419 A1 | 9/2007 | KenKnight et al. |
| 2008/0033502 A1 | 2/2008 | Harris et al. |
| 2008/0039718 A1 | 2/2008 | Drinan et al. |
| 2008/0146334 A1 | 6/2008 | Kil |
| 2008/0311968 A1 | 12/2008 | Hunter |
| 2008/0319796 A1 | 12/2008 | Stivoric et al. |
| 2009/0048070 A1 | 2/2009 | Vincent et al. |

FOREIGN PATENT DOCUMENTS

| | | |
|---|---|---|
| JP | H10-295652 | 11/1998 |
| JP | 2000-023935 | 1/2000 |
| JP | 2001-353130 | 12/2011 |
| WO | WO 9840009 A1 | 9/1998 |
| WO | WO 0015109 A1 | 3/2000 |
| WO | WO 0054237 A1 | 9/2000 |
| WO | WO 0137726 A1 | 5/2001 |

(56) References Cited

FOREIGN PATENT DOCUMENTS

| WO | WO 03009753 A2 | 2/2003 |
|---|---|---|
| WO | WO 03015005 A2 | 2/2003 |
| WO | WO 2004043246 A1 | 5/2004 |
| WO | WO 2004049937 A1 | 6/2004 |
| WO | WO 2006127719 A2 | 11/2006 |
| WO | WO 2009079366 A2 | 6/2009 |

OTHER PUBLICATIONS

Joachimowicz et al. Convergence and Stability Assessment of Newton-Kantorovich Reconstruction Algorithms for Microwave Tomography. IEEE Transactions on Medical Imaging, Aug. 1998, vol. 17, No. 4, pp. 562-570.
U.S. Appl. No. 10/032,765, Mar. 6, 2003 non-final office action.
U.S. Appl. No. 10/032,765, Dec. 4, 2003 non-final office action.
U.S. Appl. No. 10/032,765, May 18, 2004 non-final office action.
U.S. Appl. No. 10/032,765, Aug. 25, 2005 final office action.
U.S. Appl. No. 11/402,225, Sep. 29, 2009 non-final office action.
U.S. Appl. No. 11/402,225, Sep. 15, 2010 final office action.
U.S. Appl. No. 11/402,225, Apr. 13, 2011 non-final office action.
U.S. Appl. No. 11/410,519, Apr. 13, 2011 non-final office action.
U.S. Appl. No. 11/402,225, Jan. 20, 2012 final office action.
U.S. Appl. No. 11/410,519, Jan. 19, 2012 final office action.
PCT Application No. PCT/US04/27106, Feb. 18, 2005-02-18 ISR.
U.S. Appl. No. 10/922,370, Jun. 6, 2006 non-final office action.
PCT Application No. PCT/US05/31442, Jan. 24, 2006 ISR.
U.S. Appl. No. 10/922,370, Dec. 29, 2006 final office action.
U.S. Appl. No. 10/922,370, Jun. 18, 2007 non-final office action.
U.S. Appl. No. 10/922,370, May 14, 2008 final office action.
U.S. Appl. No. 11/219,327, Aug. 14, 2007 non-final office action.
U.S. Appl. No. 11/219,327, May 16, 2008 final office action.
U.S. Appl. No. 10/922,370, Aug. 3, 2009 non-final office action.
U.S. Appl. No. 11/410,519, Nov. 30, 2009 non-final office action.
U.S. Appl. No. 11/410,519, Sep. 2, 2010 final office action.
U.S. Appl. No. 11/841,947, Jan. 29, 2009 non-final office action.
U.S. Appl. No. 11/841,947, Nov. 20, 2009 final office action.
U.S. Appl. No. 11/219,348, Jan. 3, 2008 non-final office action.
U.S. Appl. No. 11/219,348, Oct. 21, 2008 final office action.
U.S. Appl. No. 11/219,348, Jan. 12, 2010 non-final office action.
U.S. Appl. No. 11/219,327, Jun. 24, 2009 non-final office action.
U.S. Appl. No. 11/219,327, Apr. 1, 2010 final office action.
U.S. Appl. No. 11/219,327, Oct. 11, 2011 non-final office action.
PCT Application No. PCT/US02/20006, May 29, 2003 ISR.
PCT Application No. PCT/US02/20006, Sep. 2, 2004 IPER.
PCT Application No. PCT/US04/27106, Feb. 21, 2006 IPRP.
PCT Application No. PCT/US05/31442, Mar. 6, 2007 IPRP.
PCT Application No. PCT/US05/31441, Mar. 6, 2007 IPRP.
U.S. Appl. No. 12/807,835, Mar. 21, 2012 non-final office action.
PCT Application No. PCT/US09/02473, Dec. 23, 2009 ISR.
PCT Application No. PCT/US09/02473, Oct. 26, 2010 IPRP.
PCT Application No. PCT/US10/02508, Apr. 22, 2011 ISR.
PCT Application No. PCT/US10/02508, Mar. 20, 2012 IPRP.
PCT Application No. PCT/US11/28160, Sep. 29, 2011 ISR.
U.S. Appl. No. 12/828,110, Oct. 13, 2011 non-final office action.
PCT Application No. PCT/US11/028160, Sep. 11, 2012 IPRP.
Australian patent application 2002365064, Nov. 17, 2006 office action.
Japanese patent application 2003-550645, Feb. 8, 2008 office action.
European patent application 02802911, Feb. 3, 2009 supplemental search report.
European patent application 04786547, Feb. 23, 2009 supplemental search report.
European patent application 02802911, Jun. 10, 2009 office action.
European patent application 04786547, Jul. 13, 2009 office action.
Australian patent application 2004266725, Aug. 10, 2009 office action.
European patent application 04786547, Jun. 29, 2010 office action.
European patent application 02802911, Sep. 29, 2010 office action.
Canadian patent application 2451526, Feb. 2, 2011 office action.
European patent application 04786547, Aug. 25, 2011 office action.
Japanese patent application 2006-524077, Sep. 6, 2011 office action.
European patent application 11174980, Sep. 29, 2011 search report.
Canadian patent application 2539547, Jan. 9, 2012 office action.
Samarati et al. Data Security. Wiley Encyclopedia of Electrical and Electronics Engineering. Dec. 27, 1999.
Jaskowski. Evaluation of the healing process of skin wounds by means of skin absolute value of electrical impedance. Dermatol. Mon.schr. 172 (1986) 223-228.
U.S. Appl. No. 11/841,947, Jul. 31, 2013 non-final office action.

\* cited by examiner

METABOLIC ENERGY MONITORING SYSTEM

CROSS REFERENCE TO RELATED PATENTS

This application claims priority under 35 U.S.C. Section 119(e) to provisional application No. 61/125,140, filed on Apr. 21, 2008; provisional application 61/134,987, filed on Jul. 16, 2008 and provisional application 61/206,423, filed on Jan. 31, 2009.

BACKGROUND OF THE INVENTION

Obesity is defined as the abnormal accumulation of body fat and is widely recognized as a significant contributing risk factor in many chronic diseases. It is well accepted that people who are obese are at significantly higher risk of heart disease, hypertension, diabetes, arthritis, and certain cancers, and consequently that obesity has direct impact on general health status and quality of life. Due to obesity's central role in determining general health and possible predisposition towards chronic diseases, there is a significant clinical and epidemiological need for the effective management of obesity.

In the management of obesity and diet, whether for the purpose of improved health, disease management or for lifestyle change, methods for the oversight of nutrition and exercise may be based upon the relationship between kilocalorie (kcal) intake and kilocalorie expenditure which yields a net energy balance (weight) for a period of time (Equation 1). If the energy balance is positive, this excess energy is typically stored within the body as a reserve source of energy, e.g. as fat, and therefore weight is gained.

$$\text{intake(kcal)} - \text{expenditure(kcal)} = \text{energy balance(kcal)} \quad \text{Equation 1.}$$

By management of an individual's overall energy balance, desired weight loss/gain or maintenance of current weight may be achieved. To accomplish this objective, a variety of approaches have been attempted. These include the use of kcal energy expenditure calculators, and estimators of kcal intake. Intake monitoring, for instance, is typically accomplished through manually maintained diaries and/or external opinions based on estimate average kcals contained in that food group or images of the actual meal. These approaches are, in general, prone to compliance or estimation error.

Alternative approaches include the use of weight scales or body composition analyzers as indices of change in overall energy balance (weight), however they do not provide feedback regarding kcal energy expenditure as compared to kcal intake. In addition, these point in time or infrequent (periodic) devices rely on user compliance that may not accurately measure kcal energy balance. Furthermore, the absence of information about any other factors associated with weight gain/loss, e.g. kcal intake, significantly limits the utility of the information as a weight management therapy.

In short, the above approaches have proven insufficient to adequately provide the data and solutions necessary to resolve the terms of Equation 1 due to poor user compliance, inherent system inaccuracies due to periodic measurements, and/or imprecision in estimation of kcal intake. What is needed is a system that enables determination of kcal energy expenditure, energy balance and kcal intake, such that useful information regarding dietary habits and kcal energy expenditure may be used to drive personalized diet and exercise plans for an individual.

SUMMARY OF THE INVENTION

The invention described herein presents a novel system for determining kcal energy expenditure, energy balance and kcal intake over a period of time. Preferred elements of the system include: at least one monitoring platform enabling the measurement of at least one physiological parameter associated with body composition, kcal intake, and/or kcal energy expenditure; at least one comparator enabling the determination of energy balance from body composition change and the determination of kcal energy expenditure, from which kcal intake may be calculated; and at least one display enabling the display of at least a portion of said determinations and calculations to the user and/or other third party.

In a preferred embodiment of the present invention, an essentially low profile and flexible monitoring platform resides in effectively continuous contact one or more body regions and provides physiological data for at least one comparator. The comparator, utilizing said physiological data, in turn determines kcal intake, kcal expenditure and energy balance and visually presents a least a portion of said determinations by means of a display located in a separate display unit, which may periodically be in wireless communication with the monitoring platform. The functions and locations of the comparator may be distributed between the monitoring platform and the display unit in order to better manage power, communication needs and processing circuitry needs between the monitoring platform and display unit.

In various embodiments, the comparator may be in communication with one or more remote data management systems, e.g. using cell phone network communication. These remote data system(s) may be provided with at least a portion of user data and, may in turn supply the user with dietary guidance, suggestions, or other forms of information. Such systems involving monitoring platforms, display units and remote data management systems are disclosed in U.S. Pat. No. 7,044,911, which is incorporated in its entirety by this reference herein. Additional information including target caloric or dietary goals, predictive trend analysis of kcal intake, caloric expenditure and/or energy balance which may enable a user to project when dietary goals will be reached may also be supplied to the user. In a variation of this embodiment, a predictive analysis is utilized by the system to automatically or upon demand provide the user corrective instructions, alerts, support, rewards, incentives, or other forms of information and services such that adherence to a dietary/exercise plan or metabolic status program may be better maintained in order to reach the desired goal. Such information may be resident within the comparator or may be provided by one or more remote data systems in communication with the comparator.

In still other embodiments, notification or communication to the user of nutritional and/or kcal energy expenditure patterns and recommendations for improvement of eating behavior or activity may be made in order to better achieve desired weight goals. Such notification may be automatically generated by the comparator or through outside parties and/or data systems in remote communication with the comparator and may consist of audible alerts, vibrations or other forms of communication either on the display unit or on the monitoring platform. In yet other embodiments, the system may provide the user access to one or more programs, counseling, and/or materials to improve their weight management. In certain instances, this access may be in the form of a menu from which the user selects the desired item.

In yet other embodiments of the invention, the system of the present invention is incorporated within a health management program involving clinician oversight for the monitoring of body metabolism or for the occurrence or progression of a disease condition.

DETAILED DESCRIPTION OF THE INVENTION

The invention generally relates to a novel system for improved weight management. The method of the system is comprised of the automatic determination of an individual's energy balance, preferably based upon measured change in body composition, and the individual's kcal energy expenditure which enables the subsequent calculation of the individual's kcal intake over a period of time. The invention further claims the use of said determined terms (balance, expenditure, intake) and factors derived from these terms for use in the management of diet and metabolic status-related health issues. In selected embodiments, one or more weight management tools may be selected by the user and/or automatically generated by algorithms associated with the system to further enable weight management goals. In addition, the present invention also may include the display, storage and transmission of said determined terms within a local or distant environment.

The system, in various embodiments, may use one or more measured physiological parameters to determine the caloric expenditure, kcal intake and energy balance status and from these values, to assist the users in modifying food intake and exercise in order to meet their targeted weight and body composition goals. The information provided to the user or other authorized third parties in these applications may include the current measured parameter status, and/or derived variables from measured/collected data such as trending or prediction when a predetermined threshold value will be exceeded. In other readily conceived embodiments, the system may be utilized for non-weight management applications, e.g. readiness or fitness monitoring of military personal and first responders, geriatric monitoring for activity and metabolic health, nutritional status monitoring, chronic disease monitoring, and possibly for use in analyte quantification such as glucose monitoring/disease treatment assessment. Accordingly, additional uses of the present invention are readily conceivable and the scope of the present invention is not limited to those applications presented herein.

Figure 1:
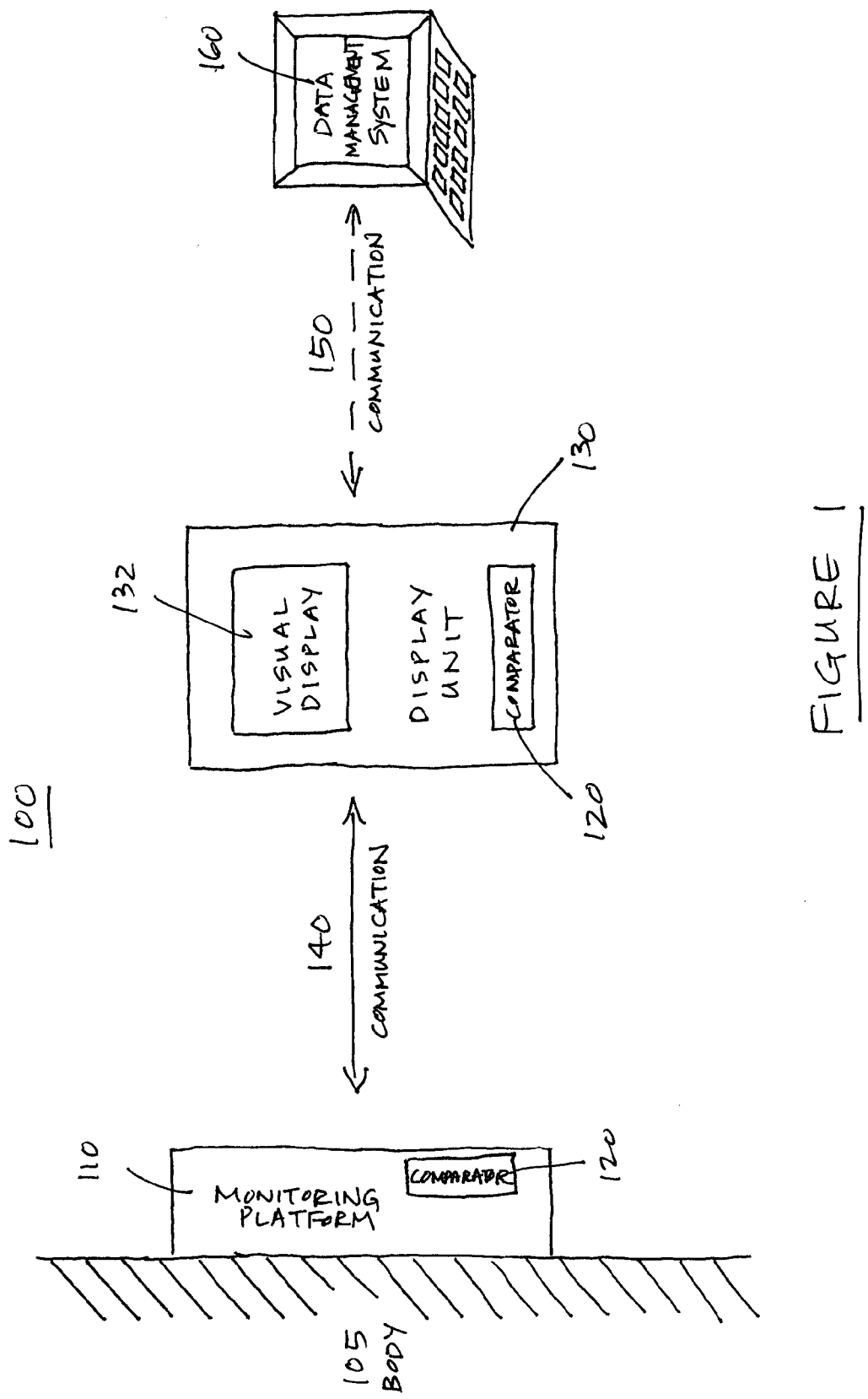
FIG. 1—Illustration of one form of the present invention.

An illustration of one form the present invention is shown in FIG. 1. As shown, system 100 consists of monitoring platform 110, in substantial contact with measured body 105. Display unit 130 has visual display 132, and comparator 120, represented by dotted line structures, is shown to reside on both monitoring platform 110 and display unit 130. Also shown is solid arrow 140 representing communication of information, instructions or data between monitoring platform 110 and display unit 130. Such communication may be by wireless, e.g. radio transmission, or direct connection means. Also shown is dashed arrow 150 representing communication between display unit 130 and one or more remote data management locations 160 which may provide additional information or data of use to the user.

According to the method of the present invention, monitoring platform 110 measures one or more physiological parameters of body 105 associated with body composition or kcal energy expenditure. Such sensed parameters may include change in tissue composition, analytes and/or fluid status. In preferred embodiments, the data from one or more measurements of one or more body regions is correlated through use of algorithms by comparator 120 to estimate change in overall body composition. Additional measurements of other physiological and/or anthropometric parameters, e.g. motion, enable determination of kcal energy expenditure of the body.

The comparator 120 also enables the storage and mathematical manipulation of said received information to determine kcal intake over a period of time, e.g. through employment of Equation 2.

$$\text{expenditure(kcal)} + \text{energy balance(kcal)} = \text{intake(kcal)} \quad \text{Equation 2.}$$

The calculated kcal intake, kcal energy expenditure and/or energy balance may then be presented to the user through use of display 130 either automatically or upon demand by the user.

The comparator 120 may also, in certain embodiments, transfer, 150, the collected data sets or information regarding energy balance, kcal expenditure, kcal intake, nutrition or other user characteristics (trends, anomalies) to a remote data management system, 160, having additional data storage and comparator functions, for additional analysis. Such transfer 150 may be by wireless or wired means, e.g. cell phone networks, ethernet communication using the internet linkages, etc. Data management system 160 may provide useful feedback to the user upon analysis of said received data, e.g. through display 130, on suggested modifications of diet, exercise or lifestyle in order to assist the user reaching their weight management targets or maintain their current energy balance (weight). In certain embodiments, trends in user data may initiate preemptive recommendations to the user by either comparator in order to mitigate or alter predicted trend outcomes.

Figure 2:
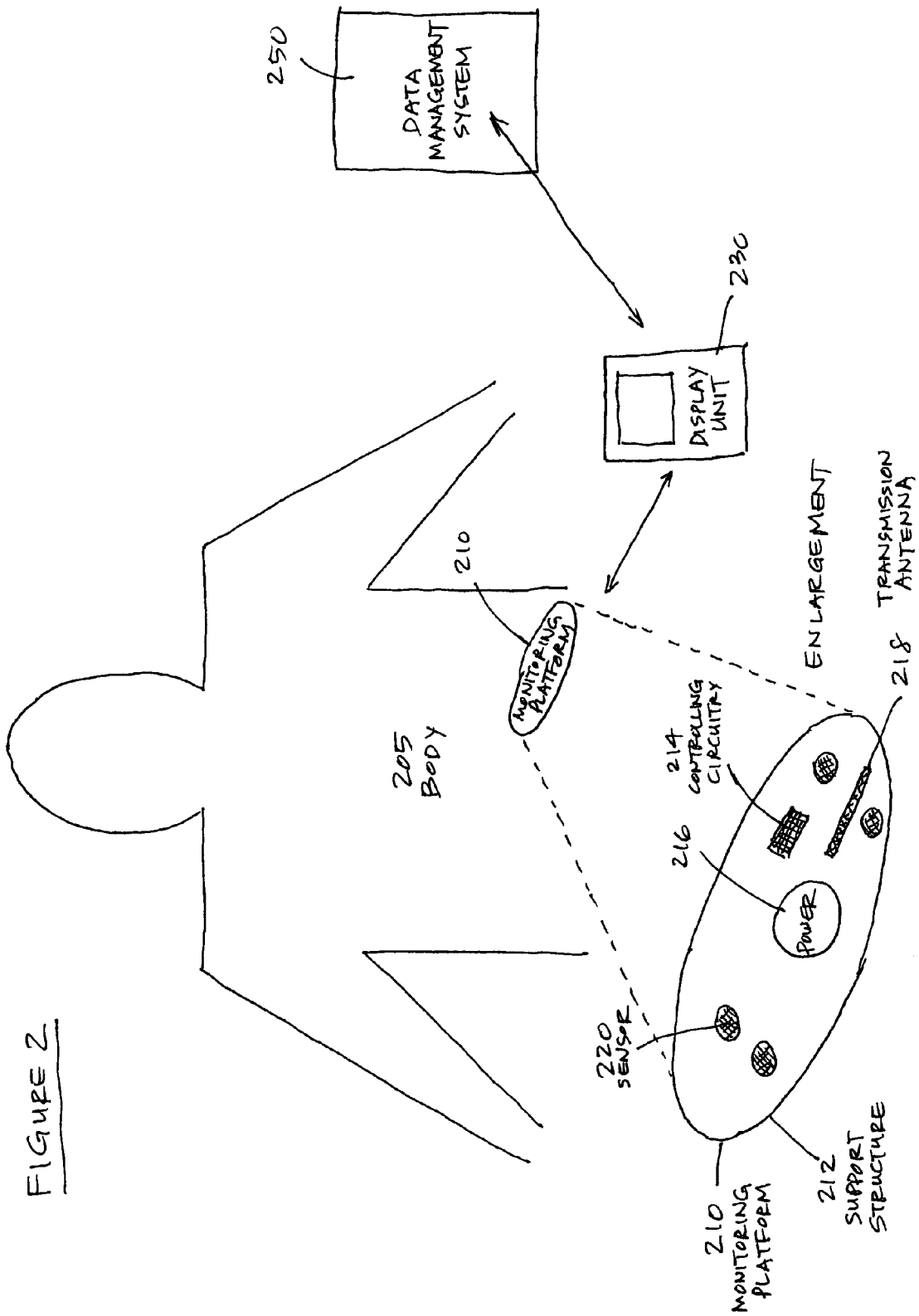
FIG. 2—Illustration of an embodiment of the present invention.

A preferred embodiment of the present invention for the purpose of weight management applications (lose and maintenance) is presented in FIG. 2. As shown, monitoring platform 210 is constructed to be substantially low profile (planar) and flexible and is affixed to body 205, at a selected body region, e.g. by means of adhesive. A patch-like monitoring platform enables possible advantageous use, e.g. enabling measurements while wearing clothing and/or ambulatory use as well as possible lowering compliance for effective employment of the system on the part of the user. A patch-like sensor also may advantageously enable measurements to be obtained from a single body region for extended periods of time, e.g. hours, days, weeks. Furthermore, effective constant contact with a single body region may advantageously afford consistency of measurements to a defined body region thereby potentially reducing unwanted variability in measured data sets taken over time due to location shift, and thereby possibly enabling a more precise determination of compositional changes occurring in the measured body region as compared to measurements taken by serial application of the measurement platform.

In order to accomplish said measurements, monitoring platform 210 has support structure 212, controlling circuitry, 214, power, e.g. battery, 216, and transmission antenna 218. Sensor elements 220 include a plurality of electrodes for conducting regional multifrequency bioelectrical impedance measurements for possible use in body composition determination, temperature sensors, e.g. thermistors, to aid in body composition and kcal energy expenditure determinations, at least one multidimensional accelerometer for possible use in kcal energy expenditure determination, and electrodes for the measurement of heart rate, also for possible use in kcal energy expenditure determination. In a variation of this preferred embodiment, at least some of the electrodes utilized for bioelectric impedance measurements may be those employed for the measurement of heart rate and respiratory rate. Not shown are necessary interconnects (wires) providing electrical connections between components and structural layers/materials providing additional layers to overall structure 210.

In further detail, controlling circuitry 214 has elements, e.g. microcontroller, memory, amplifiers, radio transceiver (transmission/reception) chipset, analog to digital converters, digital to analog converters, switches, clock crystal, etc., necessary for obtaining measurement data from sensors, processing said data, e.g. signal noise removal and conversion to values useful for subsequent analysis, and transmission of said data. Such signal manipulation and conversion into useful data represents at least a portion of the comparator's activity which may be residing on the monitoring platform. Such circuit elements may be constructed from discrete circuit components, e.g. resistors, operational amplifiers, microcontroller, or may be comprised of multifunctional components such as application specific integrated circuits (ASICs) or combinations of these elements. Such elements may also be constructed of conventional silicon-based (CMOS) circuit elements or may utilize in part or in whole, printed electronic and/or advanced nanoelectronic elements thereby enabling possibly improved platform flexibility as compared to silicon-based elements.

Figure 3:
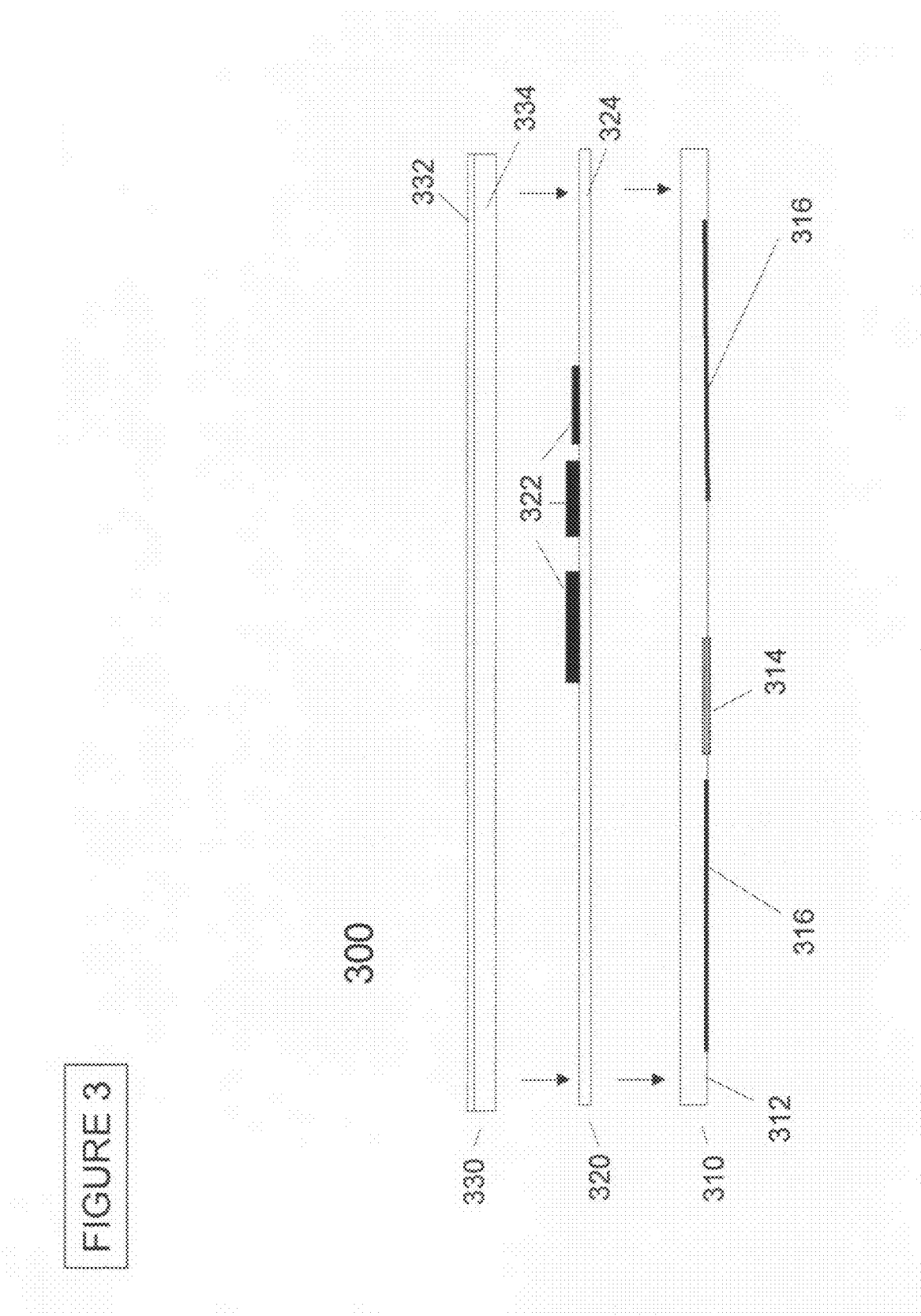
FIG. 3—Illustration of one embodiment of a monitoring platform of the present invention.

As shown in FIG. 3, the structure of the monitoring platform 300, shown in a side view with layers separated as indicated by arrows, may be comprised as a multilayered essentially low profile (planar) structure having at least three principal layers. A first layer 310, or bottom layer, has a first surface 312 enabling substantial contact with body and may include sensor elements, e.g. electrodes, 314. This layer may also include one or more biocompatible adhesives 316 to promote adherence of the monitoring platform to the body. A second or middle layer, 320, comprises the location of necessary circuitry, e.g. an electronics layer, having circuitry elements 322 necessary for monitoring platform functionality mounted on a preferably flexible substrate 324, e.g. polyimide or other suitable material. In preferred embodiments, such electronic components are constructed such that such elements are contained within the overall structure of the monitoring platform. A third, or upper layer, 330, may be comprised in large part of a protective covering 332 to minimize possible moisture contamination of underlying circuitry and sensors. In addition, the upper layer may be constructed in part of a foam material, 334, enabling improved comfort to the user. In related embodiments, the upper layer may also include one or more display elements, e.g. organic light emitting diode (OLED) display, and/or contain a logo or pattern relating to commercial or marketing purposes. The upper layer, 330, may also contain a visual indicator, e.g. light element, to confirm that the device is operating properly or has experienced an error condition.

Figure 4:
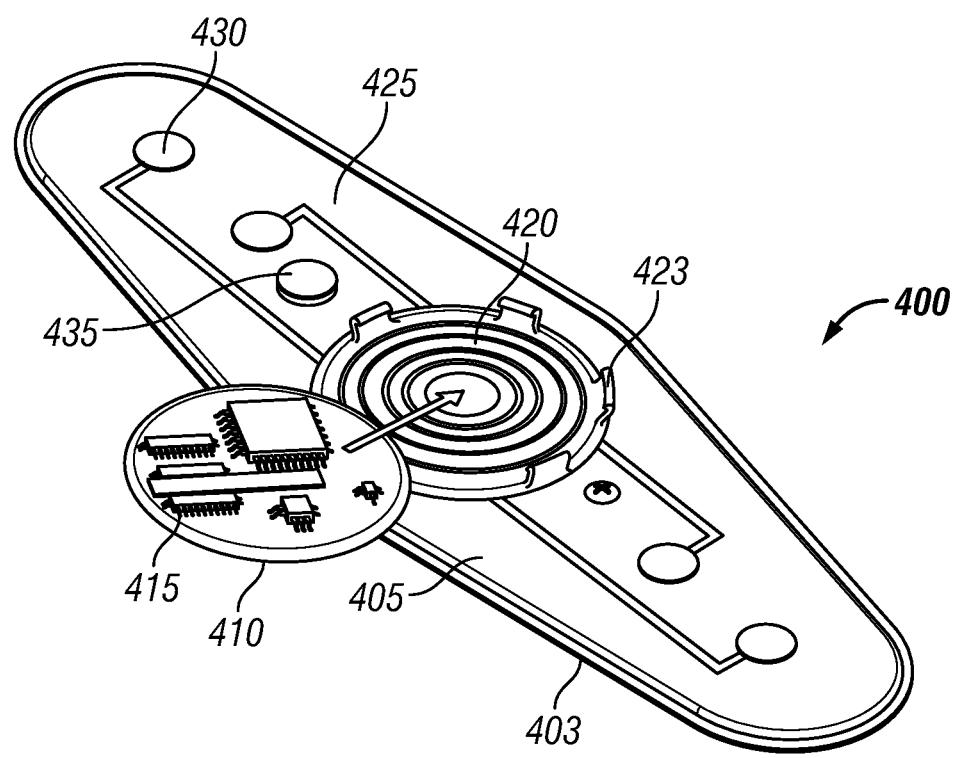
FIG. 4—Illustration of one embodiment of a monitoring platform indicating removable circuit element.

In related embodiments, portions of circuitry elements may be constructed as a removable, replaceable circuit "puck" or structure, thereby possibly lowering overall cost of monitoring platform use. One such an embodiment is shown in FIG. 4 wherein monitoring platform 400 has a substantially low profile (planar) lower structure 403 containing battery 435, sensor 430, electrical traces 425, circular electrical contacts 420 and retaining clips 423 and substantially low profile (planar) upper covering structure 405. Insertion of circuit puck 410 containing circuit elements 415 between lower structure 403 and upper structure 405 thereby enables contact between circuit puck electrical contacts located on puck 410 surface to opposing electrical contacts 420 (puck 410 electrical contacts not shown). Use of circular contacts 420 is advantageous by minimizing need for orientation requirements for correct insertion of circuit puck 410. Other geometries and forms of circuit puck structure and means of electrical contact are readily conceivable, e.g. optical interconnects, oblong shaped pucks, etc. and the scope of the present invention is not limited to the structure presented in FIG. 4.

Returning to FIG. 2, communication between monitoring platform 210 and display unit 230 in this preferred embodiment is by wireless methods, e.g. through the use radio wave communication such as BLUETOOTH® or other commonly employed radio communication means. In this preferred embodiment such communication has limited range, e.g. less than 10 meters, and may be encrypted to prevent unwanted access to transmitted data sets, etc. In other embodiments, communication between the monitoring platform 210 and display unit 230 may utilize long range radio wave communication such as cellular, WI-FI, WIMAX or other radio communication means with distances longer than 10 meters. Such communicated data may also include identifiers identifying all or a portion of the overall monitoring platform 210, e.g. circuitry 214 and/or sensors 220, such that tracking of these elements maybe enabled for a variety of useful purposes, e.g. the linking of data sets to an individual user in a larger data collection/analysis set or the tracking of manufacturing performance/reliability. In occasions where communication between monitoring platform 210 and display unit 230 is unobtainable, sensor data may be stored for a period of time, e.g. up to 24 hours, until communication is restored and sensor data may be transmitted to display unit 230.

Display unit 230 has functionalities enabling further comparator activities and conveyance of comparator information/analysis to the user such as display 232. Such functionalities (not shown) include circuitry elements, e.g. microcontroller, memory, battery, one or more transceivers and associated antenna, etc. and are well known to those skilled in the art of electronics. In certain forms of this preferred embodiment, the display unit is comprised of a cellular phone having necessary comparator software included to enable dual function as both a cell phone and as a display unit. The display unit may dynamically distribute the comparator functions between the monitoring platform 210 and display unit 230. This dynamic comparator function distribution may be adjusted based upon power supplies remaining, wireless communications link quality, measure physiological parameter rate of change or similar physiological, environmental or system elements.

Within comparator, mathematical functions, e.g. algorithms, enabling the determination of compositional change, and the resultant energy balance associated with this compositional change, kcal energy expenditure and kcal intake are present. Such algorithms may include additional information, e.g. user data such as age, gender, and/or body dimensions such as height, waist or hip size that may be input by the user or others and useful to algorithm function and comparator analysis. Such data may be input in response to queries on the display unit as part of comparator function, input through keyboard or voice recognition functions located in the display unit or input through the remote data management system 250.

Also shown in FIG. 2 is communication between display unit 230 and remote data management system 250. Such communication may involve wireless methods, e.g. through cell phone networks, combined with internet forms of communication in this preferred embodiment. At remote data management system, 250, additional analysis of user data may be performed and responses providing instructions, recommendations, support, services, etc. to better enable the user to manage weight management objectives sent back to back to display unit for the user's review.

Further details regarding each of the elements of the present invention are presented below.

Monitoring Platform—The monitoring platform consists of one or more sensors enabling the measurement of physiological parameters that are useful for the calculation of body composition, energy balance, kcal intake and kcal energy expenditure.

Body region(s) to be measured for the purpose of body composition change determination are preferably those enabling correlation to one or more measurements to changes in total body composition. More preferably, these measured regions comprise only a portion of a larger body structure, e.g. a regional measurement of a portion of the abdomen, as compared to a measurement spanning the entire torso, e.g. shoulder to hip, or extending between two extremities, e.g. leg to leg measurements. In addition, a selected region preferably enables assessment of change of one or more body composition elements e.g. body fat, body fluids, lean mass. Examples of such regions may include regions of the lower chest, abdomen, upper thigh or other body regions having significant storage of body fat responsive to changes in kilocalorie intake and expenditure.

In certain embodiments, one or more body regions may be selected as the optimal placement/measurement site based upon sensitivity of a body region to body composition change within a particular demographic group, e.g. gender, age, overall fitness (lean, normal, overweight, obese) or co-morbidities such that one group of individuals, e.g. adult males, may have a recommended placement location differing from those of a different group, e.g. adult females. Accordingly, the scope of the present invention is not limited to one body location or region.

In general terms, sensors for assessing body composition involve the exchange of one or more energies with a body region in order to enable the assessment of the composition of the body region. Such energies have in general the useful property of being differentially affected, e.g. differentially absorbed, by different tissue types and therefore analysis of signals from such sensors may be utilized to determine changes in the tissue composition through which the signal traverses.

Such sensors may include electromagnetic, electrical, optical, mechanical or acoustic energies and the scope of the present invention is not limited to any one form or type of sensor. These sensors may measure the composition, change in composition or utilize an introduced element e.g. nanopartical, photoresponsive agent, etc. to assist in these measurement activities. In a preferred form of the present invention, one or more bioelectric impedance sensors utilizing one or more frequencies generally in the range between 1 kHz and 1000 kHz, most preferably in the range between 1 kHz and 200 kHz, are utilized in the determination of body composition in one or more body regions. We have advantageously observed that regional multifrequency bioelectric measurements obtained on the lower chest/abdomen enable measurements useful for determination of factors associated with body composition and therefore useful in the system of the present invention. Such regional bioelectric impedance measurements may be adventitiously obtained using electrodes positioned in a single structure, e.g. a patch, and therefore do not require the use of wires or separate monitoring platform structures to conduct body composition measurements.

Figure 5:
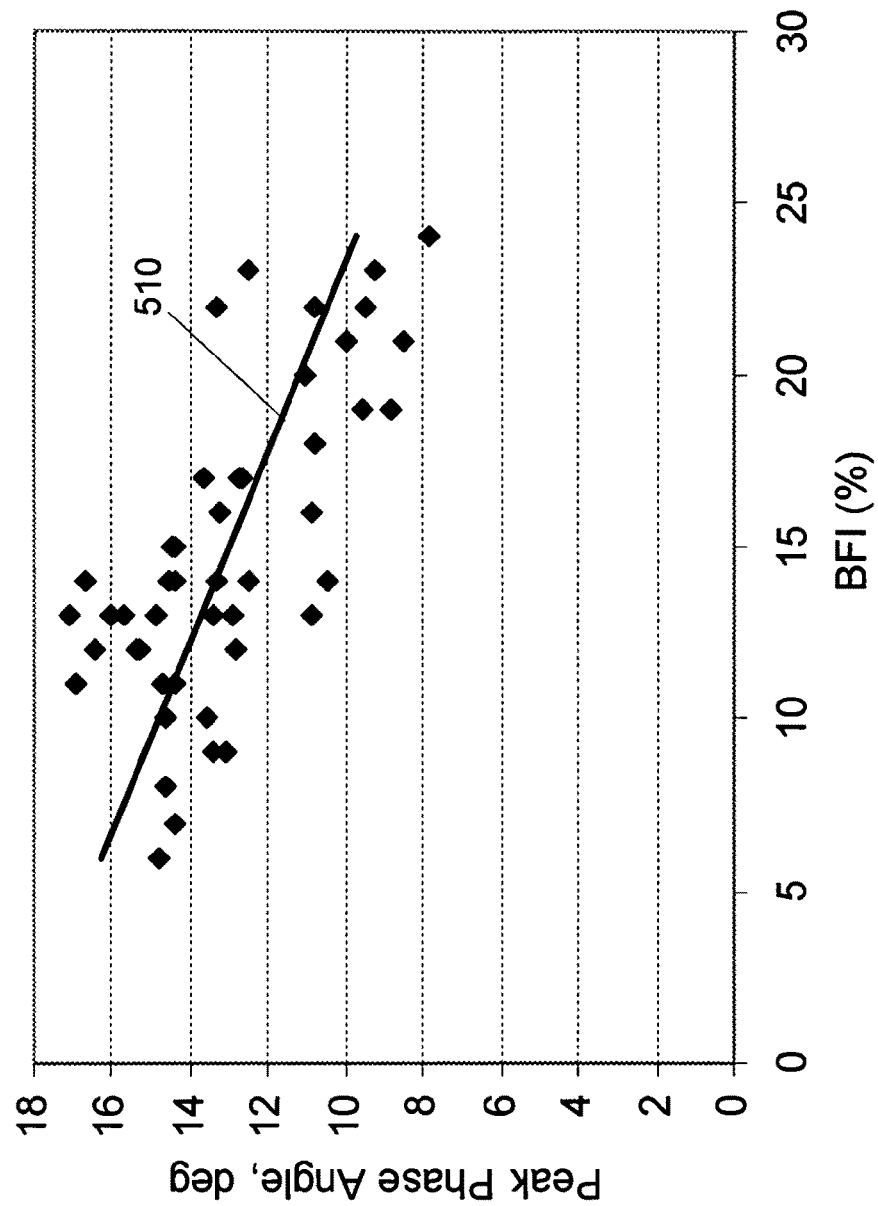
FIG. 5—Graph representing the observed relationship between body fat index and regionally measured bioelectric peak phase angle.

For example, FIG. 5 presents raw bioelectric impedance peak phase angle data obtained from such regional such regional multifrequency bioelectric impedance measurements correlated to the body fat index of multiple individuals, as measured using the published U.S. Army's body fat index algorithm. As shown by correlation line 510, there exist a significant inverse correlation between the bioelectric impedance peak phase angle and the body fat index, with a slope of $-0.4$ and correlation coefficient of $R=0.7$, thereby demonstrating general capability of measurements obtained at a body region to be correlated to body fat percentage and by extension to overall body composition. Scatter in the observed data set may be reduced and the correlation improved by the inclusion of additional factors such as gender, age, body dimensions, etc. by multiple regression or other forms of mathematical analysis. Such methods and approaches to improve correlations are well known to those skilled in the art of mathematics and body composition analysis.

In addition, sensors for determining body composition (and/or kcal energy expenditure) may be invasive, e.g. implanted. Alternatively, sensor measurements may be substantially non-invasive, e.g. through the use of electrode-type sensors in the case of impedance measurements located on the skin surface. In still other forms of the invention, completely non-contact forms of measurement may also be utilized for the determination of body composition (body fat, fluids, lean mass), analytes, kcal expenditure, or metabolic status. Examples of such forms of measurement include the use of ultra wideband radar where the exchange of one or more energies does not require direct contact with a body surface. Such ultra wideband frequencies, generally in the range between 2 GHz to 10 GHz, may provide penetration into several centimeters within body tissues and thereby may enable determination of body composition within the inspected region.

In yet other embodiments, sensors to measure one or more analytes possibly reflecting change in body composition, metabolic status or activity may be utilized either alone or in conjunction with other sensors to aid in the determination of changes in body composition, kcal expenditure, kcal intake or temporal data. Such sensors may include those for circulating hormones such as leptin or insulin, interstitial glucose, circulating lactate, circulating vitamins, exhaled ketones, exhaled carbon dioxide, nervous activity such as sympathetic nervous activity, or sensors enabling the determination of perspiration amount, composition or rate. In related embodiments, additional sensors responsive to related metabolic parameters may be included. Sensors may also include sensors reflective of long-term metabolic changes, e.g. glycosylation of blood hemoglobin, blood pressure or urine protein concentration. In form, said sensors (and monitoring platforms) may comprise structures integrated with one or more other sensors or serve as stand-alone, e.g. glucometer, sensors. Said sensors may be constructed in a variety of fashions, e.g. optical, electrical, chemical, acoustic, and utilize materials employing conventional silicon-based electronics to nanostructures to combined biological/inorganic structures, e.g. genetically engineered cells responsive to the presence of one or more analytes. The form and scope of the present invention is not limited to any one form or type of analyte sensor.

In still yet other embodiments, one or more sensors inspecting one or more body regions having same or different forms of energies may be employed to enable determination of body composition, body composition changes or metabolic status. In related forms of the invention, sensors useful for the determination of body composition changes may also utilize sensor data from other forms of body measures, e.g. weight scales, or specific gravity/buoyancy determinations, to aid in the overall analysis.

In addition to sensors for body composition determination, the method and system of the present invention may also employ one or more sensors for the determination of kcal energy expenditure. In general terms, these sensors are responsive to kcal energy expenditure of the body relating to activity. Data from such sensors may be employed in algorithms also incorporating estimations of basal/resting metabolic rate and/or other non-activity related forms kcal energy expenditure by the body, e.g. digestion, in order to determine overall kcal energy expenditure for a period of time.

In a preferred embodiment of the invention, sensors enabling the determination of kcal energy expenditure associated with activity, e.g. determination of heart rate, activity and core body temperature, are located in the same monitoring platform as those sensors employed for the determination of body composition. Forms of such sensors may include electrodes or optical means, e.g. pulse oximetry, for the determination of heart rate, multidimensional accelerometers for activity and thermistors or heat flux sensors for the determination of core body temperature. In general, the use of activity sensors and energy estimation are well known to those skilled in the art of activity measurement and, accordingly, other forms and type sensors may be employed in this regard and the scope of the present invention is not limited to one form or type of activity sensor.

One or more of the sensors utilized for kcal energy expenditure may also be utilized for body composition determination. For example, sensors enabling ultra wideband radar measurements for body composition determination may also be advantageously employed for the determination of heart rate and/or respiration rate to provide useful data for kcal energy expenditure determination. Data used for these respective analyses may be the same data sets or different. For example, regional ultra wideband radar data utilized for kcal energy expenditure determination may employ time-based measurements, such as to enable heart rate and/or respiration determination, whereas static or non-rate based data may be utilized for determination of the composition of the underlying tissue and therefore useful for body composition determination.

In alternate embodiments, sensors for kcal energy expenditure may directly correlate to the overall sum of body kcal energy expenditure, i.e. these may relate directly to overall metabolic (kcal) rate/expenditure. Such sensors may be those associated with indirect calorimetry of the body and may include those for measurement of inhale and exhaled gases, e.g. carbon dioxide exhalation relative to ambient (inhaled) levels of oxygen and carbon dioxide, or core body temperature sensors.

Sensor measurements may also be taken with varying time periods (duty cycle) commensurate with desired measured parameter, e.g. the pattern, level, or rate of activity and/or body composition status change. An example of this may be that of an activity sensor utilizing a sleep mode employing infrequent measurements, e.g. once every 10 or 30 minutes, then transitioning to an active mode, e.g. once every several seconds or few minutes, in response to a sudden change in activity or motion. As activity may vary more frequently than the rate of body composition change, the measurement duty cycle of sensor measurements for activity and/or body kcal energy expenditure determination may differ than those employed for measurement of regional composition change over a period of time.

In general form, monitoring platforms, in addition to one or more sensor elements delivering energy to or receiving energy from a body region, e.g. impedance electrodes or accelerometers, also contain electronic circuitry necessary to the proper function of the sensor(s). As such, the electronic circuitry may include: memory, microcontroller and/or digital signal processor, analog to digital converter, digital to analog converter, amplifiers and power (battery), as well as a means of communicating sensor data to one or more comparators for analysis and subsequent display. Such communication may be wireless or wired, e.g. through radio transmission or by direct connection as part of a larger circuit assembly. In certain instances, the circuitry utilized for one or more sensors, e.g. ultra wideband radar, may be utilized at least in part for communication of sensor data. In general, the design and construction of sensor circuitry are well known to those skilled in the art of electronics and, accordingly, other forms and type sensors may be employed in this regard and the scope of the present invention is not limited to one form or type of sensor circuitry. The monitoring platform may include automated activation through means such as the closing of an electrical contact, installation of a battery, exposing a photocell switch located on the platform to light, etc. In other forms, the display unit may be used to fully activate the monitoring platform from a sleep mode. This may be accomplished through a variety of means, e.g. through wirelessly transmitted instructions or through direct contact-based approaches, e.g. by use of one or more conductive elements relaying electrical signals to the monitoring platform.

In form, the sensors and monitoring platforms for body composition and/or kcal energy expenditure determination may be configured in a variety of fashions and the scope of the present invention is not limited to any one form of monitoring platform. For example, sensors may be implanted within the body, affixed directly to the skin surface, handheld, incorporated into articles of clothing, or be affixed to furniture, bedding, or attached to walls. In related embodiments, sensors of the present invention may be incorporated into medical devices having additional functions beyond those associated with the present invention.

As an example of handheld embodiment of monitoring platform, sensors may be incorporated into a handheld device also having comparator and display functionalities, e.g. within a suitably configured cell phone. In such form, sensors such as ultra wideband radar may be enabled and utilized by periodic placement of the sensors at selected body sites, e.g. against the lower chest, to provide data suitable for determination of body composition and incorporation of sensors for activity, e.g. accelerometers, within the body of the device which is intended to be worn when not in use.

In yet other embodiments, the monitoring platform(s) enabling measurement of body composition are different and physically separated from the monitoring platform (s) for measurement of kcal energy expenditure. Examples of such multiple platforms include use of pedometers or other activity sensors combined with one or more patches affixed to the body enabling measurements of body composition.

Comparator—A preferred function of the comparator is the determination of kcal energy balance, kcal expenditure and kcal intake corresponding to a period of time, e.g. hours, days or weeks. Such determination is accomplished through the use of monitoring platform data and input setup data, preferably according to the mathematical formula presented in Equation 2. It is understood that the use of kcal as energy for the purpose of calculation (and display) may be substituted for by other forms of energy unit, e.g. joules, and/or alternative forms of energy units, e.g. conversion of kcal to "cupcake" units and/or points and therefore conveyed to the user in this form, e.g. 3 cupcakes, or 3 cupcakes=7 points, to enable improved understanding and compliance to dietary regimens. Accordingly, the scope of the present invention is not constrained any one form of energy unit.

The location of the comparator functions may reside in part or in whole in electronic components located in a monitoring platform, a display unit, or in one or more remote data management systems and the system of the invention is not constrained to one location/structure for comparator activities. The dynamic allocation of the comparator functions may be controlled by the monitoring platform, display unit or remote data management system or a combination of these system elements.

At least two platform sensor data sets are preferably employed in order to accomplish the assessment of metabolic kcal parameters according to the use of Equation 2, e.g. at least one data set measured at the beginning of the specified period of time and at least one data set measured end of this period of time. Such data sets may also include a plurality of data obtained in intervening intervals within this time period. Accordingly, in such embodiments, the comparator may instruct or otherwise engage with the monitoring platform in order to accomplish the sensor measurements and receive the corresponding data sets. Such communication may include upon demand instructions issued by the comparator to the monitoring platform, or receipt of data sets from the platform taken on a preprogrammed basis by the monitoring platform. In other embodiments, projected or anticipated data sets, e.g. anticipated activity based upon past patterns of activity and/or energy balance/body composition trends may be substituted for one or more measured data sets. Accordingly, the scope of the present invention is not confined to any one form of instruction or method for obtaining said data sets to be used in this assessment.

In general, algorithms employed by the comparator for the determination of energy balance and kcal energy expenditure, kcal intake may utilize data such as user age, gender, height, fitness level, starting waist diameter and initial starting weight, to enable improved correlation of one or more regional measurements to overall body compositional change and/or net kcal energy expenditure. In certain other embodiments, other information, e.g. user or clinician inputted data such as co-morbidities, blood test results, stress test results, etc., or additional population-based data may also be included in one or more algorithms to improve determination sensitivity. In still other forms of the invention, baseline parameters are established from one or more measurements such that change or trends from this baseline(s) may be determined and employed in subsequent calculations and estimations of energy balance, calorie intake, etc.

In certain embodiments, it may not be advantageous to calculate and/or present findings associated with immediate or current status of the user. That is, such estimations do not necessarily incorporate newly ingested food or nutrients and therefore, in certain embodiments, an offset period of time, e.g. minutes or hours, may be utilized to enable distribution of ingested nutrients throughout the body prior to calculation and display.

In yet other embodiments, one or more algorithms employed for determination of energy balance and/or kcal expenditure are dynamic in that one or more parameters within said algorithms may be automatically (or manually) adjusted through use of one or more correction factors or terms inputted over time, e.g. adjustment of terms utilized in the calculation of basal metabolic rate to compensate for change in rate associated with weight loss. In related embodiments, such adjustments may include self learning or self adjustment of algorithms in response to one or more received inputs or data sets.

Kilocalorie Energy Balance In preferred embodiments of the invention, energy balance is determined from a change in body composition wherein said change in body composition is mathematically converted to corresponding energy balance (kilocalories) associated with this change. For example, if a net increase in fat of 100 g was determined, this increase may be converted to a net gain of in overall energy balance of 900 kcal using a conversion formula, e.g. 1 g fat representing approximately 9 kcal of energy.

As a preferred method of determining body composition change, the body is considered to be divided into two major compartments: body fat (BF) and fat free mass (FFM). As water content comprises ~60% of total body weight but is assumed to provide negligible contribution to the mass of fat (<2%), this observation enables the further segregation of FFM into two compartments: fluid (H) and other tissue mass (O) wherein O is comprised in part of components generally assumed to reflect the other major sources of energy within the body—lean mass—comprised of protein, e.g. muscle, and complex carbohydrates, e.g. glycogen. The remaining portion of O, e.g. bone mass, is generally considered to be invariant and non-contributing under most metabolic analysis situations. Change in the masses of protein and complex carbohydrate may in turn be converted to the overall energy balance through the use of additional conversion formula, e.g. both protein and complex carbohydrates approximately represent 4 kcal/g. From these observations, determination of change in body fat mass (BF) and other tissue mass (O) thus enables determination of overall energy balance.

Change in BF and O or components of O reflecting change in body composition and, by extension, energy balance may be derived by a number of methods and the scope of the present invention is not constrained to any one form or method. For example, change in BF and O may be accomplished through use of Equation 3 where BFI indicates the body fat index (or body fat percentage) of an individual. As general approach, the terms of Equation 3 may be determined for the initial period of measurement and subsequently at the completion of a selected time period. These two determinations thereby enabling subtraction of the initial determined values of BF and O from the final (or end of time period) values of BF and O, thereby providing the overall change in BF and O. From the change in BF and O (represented as grams or other units of mass), the energy (kcal) corresponding to these changes may then be readily determined using conversion formulas, e.g. fat=9 kcal/g and O (protein and carbohydrates)=4 kcal/g.

$$BFI = \frac{BF}{TotalBodyMass} = \frac{BF}{H + BF + O}. \qquad \text{Equation 3}$$

In preferred solutions to Equation 3, determination of BFI at the start and end of a period of time in conjunction with the determination of change in H over this period of time enables estimations of change in BF and in O, without requiring intervening or multiple weight measurements. Sensors enabling determination of BFI and H change include regional bioelectric impedance sensors wherein the resultant impedance signal is analyzed for both fluid change and body composition (BFI). Specifically, we have advantageously observed that regional bioelectric impedance resistance and reactance terms may be employed in the estimation of systemic fluid change whereas impedance phase angle terms, such as peak phase angle of multifrequency bioelectric impedance measurements, may be correlated to BFI, such as represented by data presented in FIG. 3. Utilizing these data as an example, the slope of the correlation line ($S_{BFI}$) relates the sensitivity of the change in phase angle ($\phi$) to change in BFI (Equation 4).

$$S_{BFI} = \frac{\partial(\phi)}{\partial(BFI)} = -0.4. \qquad \text{Equation 4}$$

In general terms, the smallest detectable change in bioelectric impedance phase angle enables the most sensitive determination of BFI change. The resolution of phase angle is governed by multiple factors including circuit sensitivity, number of replicate measurements, and overall signal impedance. In addition to phase angle measurements, other factors such as age, gender, lifestyle, fitness estimate, ethnicity, initial waist size, etc. may be employed in an algorithm to improve correlation between phase angle and BFI. From such inputs, an algorithm relating impedance phase angle to BFI and therefore enabling the tracking of BFI change over time may then be constructed. Likewise, algorithms for the determination of hydration change from bioelectric measurements can also be constructed and methods and devices for hydration change assessment are described in U.S. patent application Ser. No. 10/922,370, which is incorporated in its entirety by this reference herein. In general, such approaches may be employed with other forms of sensors enabling the relating of one or more regional measurements to a systemic physiological parameter e.g. body composition.

In this preferred embodiment, a first estimate of starting body mass or weight is utilized such that the initial fat mass BF may be better determined. However, since in this embodiment, the change in the components of body composition, e.g. change in BF, H and O, are utilized for subsequent use in determination of energy balance, small errors in the accuracy of inputted starting weight and overall fluid mass H do not significantly affect subsequent calculation of changes in the noted parameters.

By way of explanation, it is the accuracy of the estimation of the amount of change which is more critical to the solution of this embodiment rather than the true accuracy of the absolute masses, e.g. it is more important to determine that the change in fat is 100 g and not whether the starting fat mass was 24 kg or 24.5 kg and the resultant ending fat mass was 24.1 kg or 24.6 kg, respectively. A similar argument applies for the initial estimation of fluid H in individuals. In general, in lean individuals, H may comprise 60% of total body mass, whereas in fat individuals, H may comprise 55% or less. However, change in H for subsequent measurements contributes to overall assessment of BF and O as during the course of a day, this value may shift appreciably, e.g. several liters (or kgs), due to fluid intake and loss (urination, sweat, transpiration, etc.) whereas it is difficult for most individuals to substantially loss more than 0.1 kg of fat within this relatively short period of time. Therefore estimation of the change in H improves the overall sensitivity of the determination of the change in BF and O.

Equation 3 may then be solved for the initial or starting point of the time period by inputting sensor data corresponding to BFI and establishing a baseline fluid status, H. An estimation of starting weight may be utilized for establishing H in conjunction with population based formulas of percentage hydration corresponding to individuals of that BFI. From these initial parameters, the initial starting fat mass BF may be determined, e.g. using the form of Equation 3 utilizing total body mass in the denominator and BF in the numerator then equated to BFI. The initial starting O mass may in turn be determined by utilizing the alternate form of Equation 3 having the terms F, H and O in the denominator, BF in the numerator, and equated to BFI and solving for O upon substitution of the other terms, including a baseline fluid status H.

At the end of a selected period of time, solutions of Equation 3 for use in determining change of BF and H from initial values may be arrived at in multiple fashions. In a preferred method, sensor data corresponding to this end period is utilized to determine a new BFI corresponding to this end of period (EOP), e.g. BFIeop. Sensor data may also be used to provide data enabling change in H over this period of time to be determined, e.g. Hchange. Utilizing this determined Hchange and the initial estimate of H, a new H (Heop) may then be calculated by addition of Hchange to H. The BFIeop and Heop may then be employed in solving Equation 3 for terms of BF and O representative of the end this period time, e.g. BFeop and Oeop, respectively.

A preferred method for the determination of BFeop and Oeop is accomplished through a calculation process which includes reiteratively substituting in calculated BFeop values to determine estimates of Oeop and then employing these estimates of Oeop to arrive at further estimates of BFeop, and so on. This substitution process may be continued until convergence, e.g. no change, is observed in values of Oeop and BFeop.

An alternative is the calculation of BFeop without the simultaneous calculation of Oeop, e.g. by use of Equation 3, BFIeop, and adjusting the initial starting weight estimate by H change, and then estimate Oeop. One method for the estimation of Oeop would be to utilize results from population-based studies providing insight into the proportional loss of protein or lean mass associated with a loss of fat mass. That is, typically during dieting, approximately 70% of weight loss is associated with fat loss and 30% due to a combination of protein and carbohydrate loss. Such relationships may be employed to provide estimates of the change in O from which Oeop may be readily determined.

A yet additional method would be to consider only BF as the only parameter of interest, e.g. since fat has the highest caloric content per gram weight and is typically the focus of weight loss programs. By way of example, consider a 100 kg individual with a BFI of 25%. This BFI corresponds to a fat mass BF of 25 kg. At a second point in time, e.g. 1 or 2 days from the first determination, assume that the individual weights 101 kg, of which 0.9 kg represents added fluid (H change) and 0.1 kg in added fat mass representing a new BFI of 24.85%. The assessment of the added fat mass may be estimated according to one embodiment of the present invention through the use of measured H change and BFI measurements. That is, by use of one or more sensing methods, e.g. through the use of regional multifrequency impedance measurements, the gain in fluid may be determined. From this gain in fluid, an overall weight may be calculated to be 100.9 kg (as compared to the "true" 101 kg weight). A new BFI of the individual may also be determined through measurement, e.g. by use of bioelectric impedance phase angle measurements. As the phase angle measurement may be correlated to population-based assessments of BFI, independent of H, the measured BFI would be 24.85% (or within an error arising from the applied measurement technique). Calculating fat mass BF from the measured BFI of 24.85 and the assumed weight of 100.9 kg yields a value of BF of 25.07 kg or 0.03 kg from the "true" value. As the ability to gain or lose body fat mass is much less than the possible fluctuations associated with H over a relatively short period of time, e.g. days, such errors may be acceptable in many applications, as this error represents a fraction, e.g. 10%, of daily calorie intake.

In addition, from these calculations enabling determination of changes in the various body compartment masses, a new overall body weight estimate may be made and employed in subsequent measurements and analysis. This process may be further tailored to the individual by the use of periodic inputs of other parameters, e.g. weekly, weight scale measurements to provide further calibration of algorithm variables employed in the analysis.

Alternatively, Equation 3 may be solved and utilized in the above fashion through the inputting body weight into the comparator on two or more separate occasions, and providing to the comparator sensor data correlating to BFI on these occasions. The comparator may then utilize this information to first derive BF and subsequent, through substitution, derive an estimation of O while assuming H invariant. However, this embodiment and/or related embodiments may be adversely affected by body composition determination errors associated with non-compositional weight change resultant from fluid (hydration) change affecting the estimation of H and/or dietary/voiding patterns affecting estimation of total body weight or inaccuracies associated with temporary monitoring platform placements.

In preferred embodiments, a plurality of measurements intended for body composition analysis are taken over relatively short periods of time, e.g. seconds or minutes, such that these determinations themselves may be averaged to reduce uncertainties associated with measurement accuracies, e.g. signal noise attributable to motion artifacts and assuming that the body parameter, e.g. BF, is considered invariant during this short measurement period. These measurements in turn may be employed within larger time periods enabling determination of body composition change.

In still other embodiments of the invention, less frequent measurements may be employed, e.g. through the use of handheld monitoring platforms periodically used throughout the day. These measurements may employ one or more measurement technologies and/or one or more body sites for supplying desired data. In addition, in these as well as other embodiments of the invention, additional sensors, e.g. heart rate, respiration, temperature, etc., or sensor measurements themselves may be employed to adjust the obtained measurements to minimize signal noise, position or motion artifacts.

In short, there exist multiple approaches for the determination of body composition change and/or energy balance and the scope of the present invention is not constrained to any one form or method of solution.

In still other forms of the invention, measurements of one or more parameters reflecting an underlying physiological trait, e.g. serum glucose levels, may be combined to form a more complete indication of the overall metabolic status of an individual. These assessments may be useful in the adjustment one or more parameters within the comparator, e.g. basal metabolic rate estimation and/or body composition change associated with intake, to further tailor the described algorithm to the individual. These measured parameters may reflect both short term and long term status of the underlying physiological trait examined.

In addition, these measurements may provide insight into dietary patterns or habits not necessarily resultant in immediate body compositional change but possibly useful for guidance, instruction, etc. For instance, serum glucose levels typically rise then fall in response to ingestion of food over a period of time, e.g. minutes to hours. The pattern, duration and magnitude of such rise and fall may provide useful insight into the nature and amounts of food consumed and may be monitored by means of continuous glucose meters, etc. Therefore, the user may be supplied with relatively immediate feedback through such measures that the amount of food energy, e.g. glucose, consumed will be anticipated to result in weight loss or gain, based upon predicted kcal energy expenditure. These data may also be related to the timing of such consumption relative to kcal energy expenditure, e.g. exercise, such that more effective counseling or guidance may be provided to the user to improve overall metabolic management goals. Other metabolites in addition to glucose, e.g. circulating fatty acids, may be utilized in such fashion and therefore the scope of the present invention is not restricted to the use of glucose in this regard.

In a somewhat relate embodiment is the use of patterns or relationship between relatively short term fluctuations in serum glucose level as compared to somewhat longer term assessment of overall serum glucose levels determined through the measurement of fructosamine on a weekly level to provide a longer term, e.g. 2-3 week, assessment of possible excess serum glucose (energy) levels. A still longer assessment of overall metabolic management is provided by determination of glycohemoglobin HbA1c on a monthly or semiannual basis. These measurements when reviewed provide greater insight into daily (short term) glucose cycling as well as into the overall long term management of glucose and or other forms of kcal intake by the user and therefore may enable improved counseling, guidance, etc.

Kilocalorie Energy Expenditure In general, in preferred embodiments of the present invention, determination of kcal energy expenditure over a period of time is determined by the calculation of basal/resting metabolic rate and measured activity related kcal energy expenditure over this period of time. Of these terms, basal/resting metabolic rate is the primary component of kcal energy expenditure in individuals having sedentary or low activity lifestyles. Numerous algorithms derived from population studies are available for the estimation of this basal/resting metabolic rate and the scope of the present invention is not restricted to any one form or type of basal/resting metabolic rate determination.

In preferred embodiments, sensors enabling calculation of kcal energy expenditure associated with activity over a period of time are employed. Numerous devices and approaches may be utilized to measure activity-based kcal energy expenditure over a period of time in a more or less continuous fashion. These may include one or more technologies such as heart rate monitors, ambient temperature/humidity monitors, accelerometers, temperature monitors, heat flux monitors, sweat measurement, etc. Such methods and devices are well known to those skilled in the art of physiological energy monitoring. In preferred embodiments of the present invention, one or more such technologies are incorporated into monitoring platforms, e.g. patches, utilized for the detection of one or bioparameters useful for the determination of energy balance.

Resultant determinations of activity based kcal energy expenditure over this period of time are then combined with corresponding energy associated with basal/resting metabolic rate to arrive at a total determination of kcal energy expenditure over this period of time. As a further refinement to this and other embodiments, estimates of basal/resting metabolic rate may be adjusted to compensate for compositional changes and/or weight change over extended periods of time, e.g. weeks or months.

Energy expenditure may vary in individual, e.g. during sleep, exercising, eating, etc., and therefore one or more sensors may supply data useful in the quantification of the individual's kcal energy expenditure for one or more extended, e.g. hours or days, periods of time, and therefore in preferred embodiments sensor data is utilized in conjunction with descriptive algorithms to account for this variation. Typically, corresponding algorithms utilize additional inputted data, e.g. age, height, gender, with the data measurements of activity for determination of kcal energy expenditure. Such tracking of kcal energy expenditure throughout periods of the day enables identification of periods wherein activity may be increased or adjusted to better serve the overall goals of weight management program.

In preferred embodiment of the present invention, bioparameter monitors utilized for kcal energy expenditure, e.g. heart rate monitors, temperature sensors and accelerometers, are incorporated into the monitoring platform for determination of energy balance, e.g. sensors having bioelectric impedance and/or UWR sensing capabilities utilized in the determination of body composition change.

In yet other embodiments, kcal energy expenditure may be determined from inputted data regarding physical characteristics, e.g. age, approximate weight, height, gender, etc., and data regarding lifestyles, activity and physical history. Such embodiments may or may not use one or more devices for the direct measurement of one or more physiological parameters associated with kcal energy expenditure. In alternative embodiments, activity kcal energy expenditures may be estimated either through learned data from the individual or from population based analyses in order to arrive at a final determination of kcal energy expenditure of the user for a period of time.

In short, the scope of the invention is not constrained to any one form, device or method for the calculation of kcal energy expenditure.

Kilocalorie Energy Intake In preferred embodiments of the present invention, kcal energy intake over a period of time is calculated using Equation 2 using determinations of energy balance and kcal energy expenditure corresponding to this period of time. In variations of the present invention, multiple calculations of kcal energy intake may be made over a period of time (hours, days, weeks, etc.) such that the overall accuracy of such estimates may be improved and trends within the data set may be determined.

In alternative embodiments, estimates of kcal intake utilizing one or more measured parameters, e.g. serum or interstitial glucose measurements, are employed in conjunction with kcal energy expenditure determinations to provide an assessment of net metabolic balance over a period of time.

In still other embodiments, the comparator may also automatically or upon demand review data sets to determine trends or patterns of kcal energy expenditure, kcal intake and/or energy balance over a plurality of periods of time. Such analysis may also include the selection and presentation to the display by the comparator of one or more recommendations for achieving desired weight or metabolic status goals. Such recommendations may be incorporated in the comparator memory as part of look up tables or lists to be selected from based upon analysis of user data. In addition, such presentation to the user of one or more suggested courses of action or activity may be done a certain time points within a day such that anticipated user behavior may be modified preemptively, e.g. prompts suggesting alternatives prior to lunch to avoid excessive kcal intake. In related embodiments, such patterns may be utilized to create a "signature" for the user such that a library of such signatures may be compiled and utilized for comparisons between users or for the user over time. Such trend or pattern analysis may be accomplished in a variety of fashions, e.g. time course changes within a certain margin of error, or through self learning, artificial intelligence or neural net type programs and analysis. The scope of the present invention is not limited to any one form or method of data analysis.

In addition, metabolic information may be compiled over time to determine trends, patterns or anomalous events. Such information may be advantageously used for a variety of purposes, including the estimation of time required for attaining one or more dietary or metabolic status goals and the anticipatory prediction of energy intake or expenditure such that guidance, materials, supplies or other forms of counseling/support, may be given to alter or in support of a predicted status.

In yet further embodiments, the results of such analyses may initiate one or more therapeutic activities in order correct or assist in weight management or metabolic status objectives. Such therapeutic activities may include reminders to the user to administer one or more medications, e.g. metabolic agents such as leptin, or trigger the automatic delivery of one or more therapeutic agents. Conversely, such analyses may be useful in the adjustment of therapy, e.g. the timing and amount of delivered drugs or agents, based upon the metabolic status of the individual.

Such therapeutic activities may encompass operating in concert with one or more therapeutics devices or treatments for the management of one or more disease states, e.g. diabetes, cardiovascular disease, HIV, neuropathy, hypertension, kidney disease or metabolic syndrome. In one embodiment, forms of the present invention, implanted or non-implanted, determine in substantial measure body composition changes, net caloric balance, kcal energy expenditure and kcal intake over a period of time and then communicate with one or more therapeutic devices or systems for the treatment of a disease state. Such forms of the present invention may be comprised as separate units in direct or indirect contact with one or more therapeutic devices/systems or may be integrated within and comprise a portion of the therapeutic device/system. Examples of such therapeutic devices include, but are not limited to, devices that may alter behavior or metabolism through nerve stimulation, e.g. devices that stimulate one or more nerves to provide the sensation of satiation. Therapeutic devices may also include devices that measure one or more bioparameters, e.g. serum glucose, or devices that deliver one or more therapeutic agents, e.g. insulin delivery systems.

Multiple forms and methods of triggered responses are conceivable and the scope of the present invention is not limited to these examples.

Display Unit—In order to present energy balance, kcal energy expenditure and kcal intake data as well as additional information, e.g. suggested dietary/exercise plan changes/recommendations, to the user, one or more display units may be employed. Display units may receive this data directly or indirectly from one or more comparators. Displays may include visual images, textual messages, sounds and synthetic voices, or mechanical signals, e.g. vibrations. The means of conveying data and information within the system of the present invention is not limited to any one means or form and may change dependent upon the nature of the information being conveyed.

In addition, in certain forms of the embodiment, the display may also enable data input by the user or designated third parties. In such embodiments, input may be through one or more methods including: the use of alphanumeric keypad entry, touch pad entry, menu driven selections or voice activated software. The scope of the present invention is not limited to any one form or method of data input.

Figure 6:
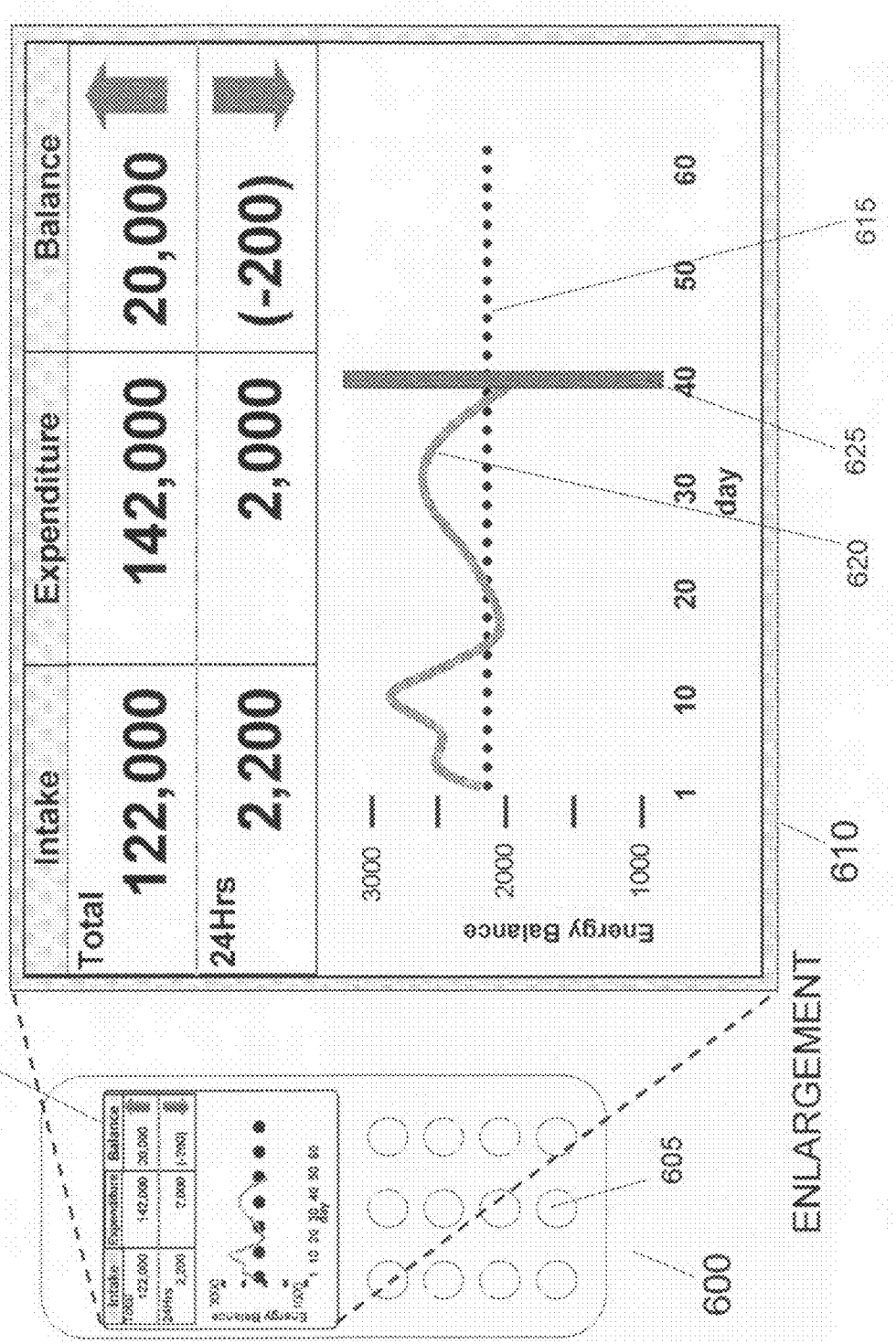
FIG. 6—Illustration of the display in one embodiment of the present invention.

An illustration of one form of the system of the present invention is shown in FIG. 6. As shown, the display 610 contained with display unit 600 presents to the user data relating both cumulative and immediately prior period of time, e.g. 24 hour rolling averages, values for kcal energy expenditure, kcal intake and energy balance. Such data may be useful to the individual as a guide to their activities, e.g. exercise and/or dietary behavior, such that weight management goals may be achieved. Also shown is a graphical illustration of the net energy balance 620 versus a predetermined weight goal 615. Also shown within this display is offset 625 wherein the metabolic parameters, e.g. kcal energy expenditure and energy intake, are not displayed for a time period indicated by the gray bar, e.g. minutes, hours or days. Use of such offset time period in display may serve multiple advantageous purposes including enabling adequate time for consumed food digestion and distribution throughout the body to occur prior to display of calculated data. Also shown are data input buttons 605 for entering useful alphanumeric information into the comparator. Use of other physiological variables, e.g. analytes (glucose), may provide an interim calculation of kcal intake while the consumed food is digested and distributed throughout the body.

In related embodiments, compositional change such as body fat percentage and percentage change over time may also be presented to the user. These data may be presented in textual, graphical or by other means and may include yet other parameters, measurements and/or data representative of the user and the history of use. In still other embodiments, the user may be presented with data, graphs or other forms of communication conveying predictive information based upon prior patterned behavior. Such predictive illustration may include options or alternatives enabling the user to view various possible scenarios and chose between these as a course of action to be followed.

In other embodiments, the display may be multilayered or multi-component. For example, in one form of the invention, the display may be a simple symbol or color, e.g. a gold star indicative of adherence within set limits of desired weight management objectives or a blue circle indicative of being beyond desired weight management limits. The user, in this embodiment, may have the ability to query the data set further, e.g. to see trend lines and/or recommendations in response to this first level display. Likewise, such symbols/display features may be incorporated within a larger display, permitting query, if so initiated by the user or qualified third party.

In yet other embodiments, the user may be presented one or more recommendations to achieve desired weight management goals from the comparator. Such recommendations may be in the forms of text messages, alert sounds, mechanical (vibrations) or combinations of these forms of delivery. These recommendations may include detailed instructions or recommendations for activity, etc. or simply serve as alerts or reminders at certain time points throughout the day. In related embodiments, the user may enter in one or more reminders or suggested course of action to be display to them at selected time points, e.g. every noontime. In related embodiments, one or more display functions may be incorporated into the structure of a monitoring platform, e.g. if the monitoring platform is physically distinct from the display unit. In such embodiments, a visual display, e.g. OLED display, audible display, mechanical (vibratory) display may be incorporated to provide the user with incentives, reminders, or other information based upon performance and/or goals. Supportive actions providing oversight in diet management while not being directly observed by others is an advantageous feature of such embodiments of the present invention.

In related embodiments, the display may incorporate an avatar or animated figure to present data, recommendations, support, etc. to the user to better enable the conveyance of desired information from the comparator to the user.

In yet other embodiments, the user may be provided through text menus, avatar-supplied search results, or by other formats, information and/or access to one or more outside services, tools, or weight management aids from which the user might select. Such services or tools include a number of possible forms, e.g. weight counseling, exercise plans/programs, diet (meal) supplies, etc. and the scope of the invention is not limited to the examples presented herein. In select embodiments, the comparator may initiate artificial intelligence-based web searchers for applicable programs, etc. tailored to the individual user's weight management profile. Such search results may then be presented by the display, including possibly through the use of one or more avatar figures.

In other forms of this embodiment, the user might be presented one or more of these options or services and upon selection, be billed by the provider for these services. In alternative embodiments, the user may have a subscription enabling use of one or more services automatically. In yet other embodiments, one or more of these services may be supplied without cost.

In a related embodiment, the user may be presented selections that have been ranked for effectiveness automatically by the data management system, e.g. the remote comparator. Such ranking may be done by multiple fashions, e.g. by other users or automatically by pooling of data derived from multiple users of the weight management system and the materials in question. Multiple forms and methods of ranking are conceivable and the method of ranking is not limited to these examples presented herein. As a further embodiment, upon selection of one or more services, plans, etc., the user may have their own data entered and available for comparison to the results from other users of the selected materials. In such circumstances, these comparisons may enable the user to determine if the selected material is effective or if their own actions are responsible for success or failure.

In still other forms of the invention, the user data is transmitted to one or more remote data management systems enabling review of user data and progress towards weight management or metabolic status goals. Such information may then be provided to clinicians, dieticians, or other third parties, including automated systems, who may assist through counseling or by other actions the individual user. In certain forms of this embodiment, the data management system provides alerts or other forms of notification to outside parties that one or more threshold criteria, e.g. diet rate or absolute values, has been exceeded and that intervention may be warranted. In such forms of the present invention, personnel communication may be enabled through the display unit between a supportive figure and the user to enable improved dietary, lifestyle and/or exercise behavior.

In selected embodiments of the present invention, rewards for goal attainment or incentives to promote compliance and/or positive activities on the part of the individual user may be provided directly by the system or through third parties with at least some access to the user through the system. Such incentives may be tangible, e.g. financial, or intangible, e.g. praise, and the present invention is not constrained to any one form of incentive and/or reward.

In certain embodiments, the user's data and/or acknowledgement of participation in the system of the present invention may be made known to other users or authorized third parties. Such data/acknowledgement may be presented in a variety of formats or methods, e.g. internet based virtual reality sites utilizing avatars representative of individual system users and/or other third parties (trainers, coaches or clinicians), text messaging, or real time internet based video discussion groups. A benefit from such interactions may be socialization of the user within a support network which may positively reinforce the user's involvement with weight or metabolic management programs, plans or activities. As an extension of such embodiments, the system may engage with one or more outside sources to enable the automatic ordering and/or delivery of items useful to the user, e.g. dietary supplements, prepackaged meals, or motivational media, and may be based in part upon user data.

Methods by which one or more embodiments of the present invention may communicate with remote data management systems and/or the internet may be by wired or wireless means. In a preferred form of the invention, the comparator and display are contained within a wireless cellular phone thereby enabling remote communication through wireless network communication capabilities.

In addition, the present invention may be used in conjunction with one or more additional medical systems or devices to improve the management of care for patients utilizing these systems or devices or to improve the function of these systems or devices. Examples of such systems may be those systems providing satiation control, e.g. through nerve activation or automated delivery of one or more drugs or therapies, or in the management of metabolic syndrome involving at least in part the measurement of serum or interstitial glucose levels.

Overall, the scope of the present invention is not limited to the examples presented herein. Additional forms of the invention are readily conceivable as well as are forms of the invention involving various combinations of the embodiments presented herein and therefore are within the scope of the present invention.

EXAMPLES OF USE

The method and system of the present invention may be employed for a variety of uses and applications. Such applications may range from individual users managing body weight to achieve desired weight goals to clinical/nursing home applications to ensure adequate nutrition by geriatric patients. Still other applications of the present invention employ the method and devices of the present invention to monitor metabolic status and/or derived components of metabolic status, such as glucose levels.

Example A) Weight Management System. In this example, the system of the present invention is comprised of two user enabled devices: an on-body monitoring patch for the measurement of bioparameters and/or physiological characteristics enabling determination of body composition change and kcal energy expenditure and a display unit in wireless communication with one or more on-body monitoring patches. The display unit in turn is in communication with at least one remote data management system through wireless means. In this example, the display unit (and the preponderance of comparator activities as well as data input features) of the system are contained within a cell phone such that the electronic functionalities of the phone, e.g. logic circuitry, memory and battery power, also enable the data collection, analysis and display functions of the present invention.

To utilize the system according to this example, a user first activates the system. Activation of the system may, in one form, be accomplished through the dialing of the cell phone to connect to a remote data management service for enrollment into the weight management system. The data management service, in turn, may download software and/or weight management system service options to the user's cell phone which is also employed as the comparator/display device.

In conjunction with enrollment, the user activates a monitoring platform for use in the determination of body composition and kcal energy expenditure. Such activation may comprise the closing of an electrical contact, installation of a battery, exposing a photocell switch located on the platform to light, etc. System activation may also include inputting data to a comparator located within the cell phone. This input may include use of the cell phone keypad, or use of verbal/voice recognition software. This inputted data may include an identifier of the monitoring platform to enable authentication/decryption of user data and the synching of the cell phone to the monitoring platform. Additional inputted data may include useful information for comparator algorithm use such as age, weight, gender, waist size and desired weight goal.

In use, the monitoring platform, in the form of as adhesive patch, is continually worn on the body, and wirelessly communicates with the cell phone/display in a periodic fashion, e.g. every few minutes. When the cell phone is out of range of the patch, the sensor data is stored in memory on the patch then downloaded to the cell phone when communication is restored. In this example, communication between the monitoring platform and the cell phone may be accomplished through wireless transmission means such as BLUETOOTH or Ultra Wideband radio.

After an initial period, e.g. 1-24 hours, the display may present the user with their kcal expenditure, energy balance and kcal intake values. This presentation may be continually updated, e.g. hourly, such that a rolling 24 hour average is continually presented to the user. After several days of use, patterned behavior and trends relative to goals may be determined by the comparator and displayed to the user. In addition, one or more suggestions may be relayed to the user to either encourage their existing activities/diet habits or suggest alterations to reach weight management goals.

After a period of use, e.g. one week, the patch may be removed, and a new patch positioned on the body. Previous data from the prior patch remains stored within the comparator enabling calibration of the new patch readings without the need to re-enter data or loss of the prior data. In one form of this embodiment, the sensor data from the old patch enables the automatic identification of the user and may enable full activation of the replacement patch without the need to re-input other data, e.g. identifiers associated with the replacement patch, etc.

Through the cell phone, the comparator may also initiate internet browsing or menus to enable the user to select from available options to support their weight management goals through the remote data management service.

In a related form of this embodiment, some or all the sensors, e.g. body composition sensors and activity sensors, are contained within the cell phone such that the on-body monitoring is primarily restricted to waking hours when the cell phone is carried by the user.

Example B) Geriatric Dietary Management System. In this example, one or more bioparameter monitoring devices are affixed to, e.g. sensor patches, or otherwise collect data from monitored individuals and wirelessly communicate with one or more fixed data collection units, e.g. wall mounted units, located throughout an assisted care facility. Data from said data collection units are then compiled at a central receiving station, e.g. a nursing station, and through the use of one or more identifiers associated with the bioparameter monitoring devices, enables the calculation and display of overall energy balance, kcal expenditure and kcal intake for each specific individual.

In such embodiments, displays of other bioparameters, e.g. activity, as well as recommendation, e.g. adjustment of levels of activity, may be incorporated into displays. In addition, alerts indicating when clinician or system set limits are achieved or exceeded may also be included. Extensions of such embodiments may also include transmission of data and/or transforms of the data to one or more remote data management systems enabling remote clinician review and bidirectional communication with either the individual's monitoring platform and/or the central receiving station.

Example C) Metabolic Status Monitoring System. In this form of the present invention, the sensors and system of the present invention are utilized to provide estimations of one or more metabolic processes and/or analyte levels. In one variation of this embodiment, estimations of circulating blood glucose levels are made. Such estimates may be done through estimates of kcal energy expenditure and/or nervous activity, e.g. sympathetic nerve activity, and may utilize data from sensors such as heart rate, temperature, sweat, nerve monitors, and/or activity. In addition, estimation of glucose may be further refined by use of one or more measures of body composition and/or net energy balance. In such implementations, the comparator/display may be a handheld unit also having the ability to utilize additional physiological sensor inputs, e.g. blood strip tests, in addition to the data received from one or more monitoring platforms. In addition, other sensors may be utilized to supply information regarding analyte levels, e.g. circulating leptin or glucose levels, such that a more complete analysis of body composition, energy metabolism and/or metabolic status may be made by the comparator.

Example D) Training and Fitness Assessment. The method and system of the present invention may be used to assess the overall fitness of individuals as to their metabolic status and/or body composition. Such assessments may be useful for individuals engaged in strenuous activities, e.g. military personnel, first responders, athletes, or individuals to whom physical appearance and fitness are important criteria for their occupation, e.g. fashion industry workers, or models. In particular, in such applications, the system may be triggered by fat mass loss below a preset level or at an unacceptable rate indicative of poor or inadequate nutrition or of excessive dieting. Conversely, the system may be employed to monitor individuals as they progress through a fitness or training regimen, enabling the monitoring of body fat loss and the tailoring of caloric (food) supplements to better fit dietary needs.

Extension of the present invention to other applications may include the monitoring of one or more physiological parameters that may indicate the status of a measured subject's nutritional or metabolic condition or the detection of one or more physiological anomalies indicative of injury or trauma. A variety of applications, based upon the present invention, are readily conceivable and the scope of the invention is not limited to the examples presented above.

What is claimed is:

1. A method for determining a metabolic status over a period of time, the method comprising:
    using a sensor to make at least one determination of a body composition change encompassing said period of time;
    making at least one determination of a kcal energy expenditure encompassing said period of time; and
    making at least one determination of an energy intake corresponding to said period of time;
    wherein the determination of the body composition change includes a determination of a fluid mass change, and
    wherein said determination of the body composition change is utilized by circuitry for a determination of an energy balance corresponding to said period of time, and wherein the determination of the energy balance does not include the fluid mass change, and
    wherein the determination of said energy balance is utilized in conjunction with the determination of the kcal energy expenditure in making the determination of the energy intake.

2. The method of claim 1 wherein the period of time is hours, days or weeks.

3. The method of claim 1 further comprising trending or patterning the metabolic status over multiple periods of time using the determination of the energy intake.

4. A system for determining a metabolic status of a user over a period of time, the system comprising:
    a) at least one monitoring platform for making at least one measurement of at least one physiological parameter;
    b) at least one comparator for making a determination of a body composition change and a kcal energy expenditure over said period of time; and
    c) and at least one display unit for displaying at least a portion of said determination;
    wherein the determination of the body composition change includes a determination of a fluid mass change, and
    wherein said measurements are utilized by the comparator for the determination of the body composition change for said period of time, then subsequently employed by the comparator for an automatic determination of an energy balance which does not include the fluid mass change, and
    wherein the determination of the energy balance in conjunction with the determination of the kcal energy expenditure enables a determination of a kcal energy intake.

5. The system of claim 4 wherein said monitoring platform is configured to be affixed to a body region and enables ambulatory activities by the user while being affixed over the period of time.

6. The system of claim 4 wherein said monitoring platform and said display unit are incorporated into a handheld device.

7. The system of claim 4 further comprising a data management system in communication with said comparator and said display unit.

8. The system of claim 7 wherein the data management system is capable of presenting one or more weight management aids or tools to the user.

9. The system of claim 4 wherein the display is capable of displaying one or more incentives or rewards to the user in response to determined parameters.

10. A system for automatically determining a body composition change over a period of time, the system comprising:
    a) at least one monitoring platform for making a measurement in at least one body region of one or more physiological parameters associated with the body composition change, the body composition change including a fluid mass change; and b) at least one comparator for utilizing the measurement to automatically determine the body composition change corresponding to said period of time which does not include the fluid mass change.

11. The system of claim 10 wherein said monitoring platform is configured to be affixed to said body region over said period of time and is configured for ambulatory use.

12. The system of claim 11 wherein said monitoring platform makes the measurement automatically while affixed to said body region over said period of time.

13. The method of claim 1, wherein the sensor includes an impedance sensor.

14. The method of claim 13, wherein the impedance sensor is capable of measuring one or more of an impedance resistance, and an impedance reactance, and an impedance phase angle at one or more frequencies.

15. The method of claim 1, wherein the sensor includes an ultra-wideband radio (UWR) sensor.

16. The method of claim 1, wherein the determination of the fluid mass change includes using a population-based formula.

17. The method of claim 1, wherein the determination of the body composition change further includes a determination of a body fat change and a determination of a lean mass change.

18. The method of claim 17, wherein the determination of the body fat change and the determination of the lean mass change include using a reiterative substitution process.

19. The method of claim 17, wherein the determination of the body fat change and the determination of the lean mass change include using a ratio from population-based studies.

20. The method of claim 17, wherein the lean mass change is ignored.

21. A method for automatically determining a body composition change over a period of time, the method comprising:

using a sensor to make a measurement in at least one body region of one or more physiological parameters associated with the body composition change, the body composition change including a fluid mass change; and using circuitry to utilize the measurement to determine the body composition change corresponding to said period of time which does not include the fluid mass change.

\* \* \* \* \*